(12) United States Patent
Agrawal et al.

(10) Patent No.: US 10,314,463 B2
(45) Date of Patent: Jun. 11, 2019

(54) AUTOMATED ENDOSCOPE CALIBRATION

(71) Applicant: Auris Health, Inc., Redwood City, CA (US)

(72) Inventors: Varun Agrawal, Mountain View, CA (US); Atiyeh Ghoreyshi, Richmond, CA (US); David S. Mintz, Mountain View, CA (US)

(73) Assignee: Auris Health, Inc., Redwood City, CA (US)

( * ) Notice: Subject to any disclaimer, the term of this patent is extended or adjusted under 35 U.S.C. 154(b) by 39 days.

(21) Appl. No.: 15/191,391

(22) Filed: Jun. 23, 2016

(65) Prior Publication Data

US 2016/0374541 A1 Dec. 29, 2016

Related U.S. Application Data

(60) Provisional application No. 62/185,135, filed on Jun. 26, 2015.

(51) Int. Cl.
*A61B 1/00* (2006.01)
*A61B 34/30* (2016.01)
(Continued)

(52) U.S. Cl.
CPC ...... *A61B 1/00149* (2013.01); *A61B 1/00006* (2013.01); *A61B 1/00009* (2013.01);
(Continued)

(58) Field of Classification Search
CPC ... A61B 34/30; A61B 34/37; A61B 2034/301; A61B 2034/2061; A61B 1/00057; A61B 1/00149; A61B 34/20; A61B 2017/00725
See application file for complete search history.

(56) References Cited

U.S. PATENT DOCUMENTS 4,644,237 A 2/1987 Frushour et al.
4,748,969 A 6/1988 Wardle
(Continued)

FOREIGN PATENT DOCUMENTS

DE 102013100605 7/2014
EP 1 566 150 8/2005
(Continued)

OTHER PUBLICATIONS

Kukuk, Oct. 5, 2001, TBNA-protocols: Guiding TransBronchial Needle Aspirations Without a Computer in the Operating Room, MICCAI 2001, 2208:997-1006.
(Continued)

*Primary Examiner* — Alexandra L Newton
(74) *Attorney, Agent, or Firm* — Knobbe Martens Olson & Bear LLP

(57) ABSTRACT

A surgical robotic system automatically calibrates tubular and flexible surgical tools such as endoscopes. By accounting for nonlinear behavior of an endoscope, the surgical robotic system can accurately model motions of the endoscope and navigate the endoscope while performing a surgical procedure on a patient. The surgical robotic system models the nonlinearities using sets of calibration parameters determined based on images captured by an image sensor of the endoscope. Calibration parameters can describe translational or rotational movements of the endoscope in one or more axis, e.g., pitch and yaw, as well as a slope, hysteresis, or dead zone value corresponding to the endoscope's motion. The endoscope can include tubular components referred to as a sheath and leader. An instrument device manipulator of the surgical robotic system actuates pull wires coupled to the sheath or the leader, which causes the endoscope to articulate.

14 Claims, 28 Drawing Sheets

(51) Int. Cl.
*A61B 1/005* (2006.01)
*A61B 90/00* (2016.01)

(52) U.S. Cl.
CPC .......... *A61B 1/0016* (2013.01); *A61B 1/0052* (2013.01); *A61B 1/00057* (2013.01); *A61B 34/30* (2016.02); *A61B 2034/301* (2016.02); *A61B 2090/064* (2016.02)

(56) References Cited

U.S. PATENT DOCUMENTS

| | | |
|---|---|---|
| 5,280,781 A | 1/1994 | Oku |
| 5,408,263 A | 4/1995 | Kikuchi |
| 5,672,877 A | 9/1997 | Liebig et al. |
| 5,899,851 A | 5/1999 | Koninckx |
| 6,004,016 A | 12/1999 | Spector |
| 6,198,974 B1 | 3/2001 | Webster, Jr. |
| 6,246,200 B1 | 6/2001 | Blumenkranz et al. |
| 6,459,926 B1 | 10/2002 | Nowlin |
| 6,837,846 B2 | 1/2005 | Jaffe |
| 7,197,354 B2 | 3/2007 | Sobe |
| 7,607,440 B2 | 10/2009 | Coste-Maniere et al. |
| 7,772,541 B2 | 8/2010 | Froggatt et al. |
| 8,335,557 B2 | 12/2012 | Maschke |
| 8,396,595 B2 | 3/2013 | Dariush |
| 8,442,618 B2 | 5/2013 | Strommer et al. |
| 8,506,555 B2 | 8/2013 | Ruiz Morales |
| 8,554,368 B2 | 10/2013 | Fielding et al. |
| 8,720,448 B2 | 5/2014 | Reis et al. |
| 8,738,181 B2 | 5/2014 | Greer et al. |
| 8,827,948 B2 | 9/2014 | Romo et al. |
| 8,929,631 B2 | 1/2015 | Pfister et al. |
| 8,945,095 B2 | 2/2015 | Blumenkranz |
| 9,014,851 B2 | 4/2015 | Wong et al. |
| 9,057,600 B2 | 6/2015 | Walker et al. |
| 9,129,417 B2 | 9/2015 | Zheng et al. |
| 9,199,372 B2 | 12/2015 | Henderson et al. |
| 9,226,796 B2 | 1/2016 | Bowling |
| 9,256,940 B2 | 2/2016 | Carelsen et al. |
| 9,289,578 B2 | 3/2016 | Walker et al. |
| 9,314,306 B2 | 4/2016 | Yu |
| 9,345,456 B2 | 5/2016 | Tsonton et al. |
| 9,358,682 B2 | 6/2016 | Ruiz Morales |
| 9,504,604 B2 | 11/2016 | Alvarez |
| 9,561,083 B2 | 2/2017 | Yu et al. |
| 9,622,827 B2 | 4/2017 | Yu |
| 9,629,595 B2 | 4/2017 | Walker et al. |
| 9,675,422 B2 | 6/2017 | Hourtash et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,789,608 B2 | 10/2017 | Itkowitz et al. |
| 9,844,353 B2 | 12/2017 | Walker et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 2002/0161280 A1 | 10/2002 | Chatenever et al. |
| 2003/0045778 A1 | 3/2003 | Ohline |
| 2003/0182091 A1 | 9/2003 | Kukuk |
| 2004/0257021 A1 | 12/2004 | Chang et al. |
| 2005/0043718 A1 | 2/2005 | Madhani |
| 2005/0065400 A1 | 3/2005 | Banik |
| 2005/0256398 A1 | 11/2005 | Hastings |
| 2005/0261551 A1* | 11/2005 | Couvillon, Jr. .... A61B 1/00059 600/118 |
| 2006/0015096 A1 | 1/2006 | Hauck et al. |
| 2006/0041293 A1 | 2/2006 | Mehdizadeh |
| 2007/0013336 A1 | 1/2007 | Nowlin et al. |
| 2007/0043455 A1 | 2/2007 | Viswanathan |
| 2007/0135886 A1 | 6/2007 | Maschke |
| 2007/0150155 A1 | 6/2007 | Kawai |
| 2007/0249911 A1 | 10/2007 | Simon |
| 2007/0253599 A1 | 11/2007 | White et al. |
| 2007/0287992 A1 | 12/2007 | Diolaiti |
| 2007/0299353 A1 | 12/2007 | Harlev et al. |
| 2008/0108870 A1 | 5/2008 | Wiita et al. |
| 2008/0123921 A1 | 5/2008 | Gielen et al. |
| 2008/0140087 A1 | 6/2008 | Barbagli et al. |
| 2008/0159653 A1 | 7/2008 | Dunki-Jacobs et al. |
| 2008/0231221 A1 | 9/2008 | Ogawa |
| 2008/0249640 A1 | 10/2008 | Vittor et al. |
| 2008/0255505 A1 | 10/2008 | Carlson |
| 2008/0312771 A1 | 12/2008 | Sugiura |
| 2009/0076534 A1 | 3/2009 | Shelton |
| 2009/0184825 A1 | 7/2009 | Anderson |
| 2009/0198298 A1 | 8/2009 | Kaiser et al. |
| 2009/0245600 A1 | 10/2009 | Hoffman |
| 2009/0287354 A1 | 11/2009 | Choi |
| 2010/0030115 A1 | 2/2010 | Fujimoto |
| 2010/0076263 A1* | 3/2010 | Tanaka ............... A61B 1/00006 600/109 |
| 2010/0121138 A1 | 5/2010 | Goldenberg et al. |
| 2010/0234856 A1 | 9/2010 | Stoianovici et al. |
| 2010/0256812 A1 | 10/2010 | Tsusaka et al. |
| 2011/0082462 A1 | 4/2011 | Suarez |
| 2011/0137122 A1 | 6/2011 | Kawai |
| 2011/0153252 A1 | 6/2011 | Govari |
| 2011/0160570 A1 | 6/2011 | Kariv |
| 2011/0196199 A1 | 8/2011 | Donhowe et al. |
| 2011/0319910 A1 | 12/2011 | Roelle et al. |
| 2012/0000427 A1 | 1/2012 | Nilsson |
| 2012/0046522 A1 | 2/2012 | Naito |
| 2012/0059249 A1 | 3/2012 | Verard et al. |
| 2012/0071752 A1 | 3/2012 | Sewell |
| 2012/0071822 A1 | 3/2012 | Romo et al. |
| 2012/0123441 A1 | 5/2012 | Au |
| 2012/0209293 A1 | 8/2012 | Carlson |
| 2012/0215094 A1 | 8/2012 | Rahimian et al. |
| 2012/0253276 A1 | 10/2012 | Govari |
| 2012/0328077 A1 | 12/2012 | Bouvier |
| 2013/0090530 A1* | 4/2013 | Ramamurthy ........... A61B 5/06 600/182 |
| 2013/0102846 A1 | 4/2013 | Sjostrom |
| 2013/0131503 A1 | 5/2013 | Schneider et al. |
| 2013/0165854 A1 | 6/2013 | Sandhu et al. |
| 2013/0165945 A9 | 6/2013 | Roelle |
| 2013/0325030 A1 | 12/2013 | Hourtash et al. |
| 2014/0114180 A1 | 4/2014 | Jain |
| 2014/0135985 A1 | 5/2014 | Coste-Maniere et al. |
| 2014/0142591 A1 | 5/2014 | Alvarez et al. |
| 2014/0163664 A1 | 6/2014 | Goldsmith |
| 2014/0222207 A1 | 8/2014 | Bowling et al. |
| 2014/0264081 A1 | 9/2014 | Walker et al. |
| 2014/0296870 A1 | 10/2014 | Stern et al. |
| 2014/0309649 A1 | 10/2014 | Alvarez et al. |
| 2014/0316420 A1 | 10/2014 | Ballard et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0051592 A1 | 2/2015 | Kintz |
| 2015/0088161 A1 | 3/2015 | Hata |
| 2015/0101442 A1 | 4/2015 | Romo |
| 2015/0104284 A1 | 4/2015 | Riedel |
| 2015/0119628 A1 | 4/2015 | Bharat et al. |
| 2015/0119637 A1 | 4/2015 | Alvarez et al. |
| 2015/0119638 A1 | 4/2015 | Yu et al. |
| 2015/0164594 A1 | 6/2015 | Romo et al. |
| 2015/0164595 A1 | 6/2015 | Bogusky |
| 2015/0164596 A1 | 6/2015 | Romo |
| 2015/0202015 A1 | 7/2015 | Elhawary |
| 2015/0223902 A1 | 8/2015 | Walker et al. |
| 2015/0265359 A1 | 9/2015 | Camarillo |
| 2015/0335480 A1 | 11/2015 | Alvarez et al. |
| 2015/0342695 A1 | 12/2015 | He |
| 2015/0359597 A1 | 12/2015 | Gombert et al. |
| 2015/0374956 A1 | 12/2015 | Bogusky |
| 2016/0001038 A1 | 1/2016 | Romo et al. |
| 2016/0005168 A1 | 1/2016 | Merlet |

(56) References Cited

U.S. PATENT DOCUMENTS

| | | |
|---|---|---|
| 2016/0005220 A1 | 1/2016 | Weingarten |
| 2016/0005576 A1 | 1/2016 | Tsukamoto |
| 2016/0016319 A1 | 1/2016 | Remirez |
| 2016/0045269 A1 | 2/2016 | Elhawary et al. |
| 2016/0051221 A1 | 2/2016 | Dickhans et al. |
| 2016/0066794 A1 | 3/2016 | Klinder et al. |
| 2016/0073928 A1 | 3/2016 | Soper |
| 2016/0081568 A1 | 3/2016 | Kolberg |
| 2016/0100772 A1 | 4/2016 | Ikuma |
| 2016/0184032 A1 | 6/2016 | Romo |
| 2016/0228032 A1 | 8/2016 | Walker et al. |
| 2016/0270865 A1 | 9/2016 | Landey et al. |
| 2016/0270866 A1 | 9/2016 | Yu |
| 2016/0278865 A1 | 9/2016 | Capote |
| 2016/0287111 A1 | 10/2016 | Jacobsen |
| 2016/0287279 A1 | 10/2016 | Bovay et al. |
| 2016/0287840 A1 | 10/2016 | Jiang |
| 2016/0296294 A1 | 10/2016 | Moll et al. |
| 2016/0331469 A1 | 11/2016 | Hall et al. |
| 2016/0338787 A1* | 11/2016 | Popovic ............. A61B 1/00057 |
| 2016/0346924 A1 | 12/2016 | Hasegawa |
| 2016/0354057 A1 | 12/2016 | Hansen et al. |
| 2016/0360947 A1* | 12/2016 | Iida .................... A61B 1/00009 |
| 2016/0360949 A1 | 12/2016 | Hyodo |
| 2016/0374541 A1 | 12/2016 | Agrawal et al. |
| 2017/0007337 A1 | 1/2017 | Dan |
| 2017/0056215 A1 | 3/2017 | Nagesh et al. |
| 2017/0065357 A1 | 3/2017 | Schuh |
| 2017/0065363 A1 | 3/2017 | Schuh |
| 2017/0065364 A1 | 3/2017 | Schuh |
| 2017/0065365 A1 | 3/2017 | Schuh |
| 2017/0068796 A1 | 3/2017 | Passerini et al. |
| 2017/0100199 A1 | 4/2017 | Yu |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0151027 A1 | 6/2017 | Walker et al. |
| 2017/0165011 A1 | 6/2017 | Bovay et al. |
| 2017/0165503 A1 | 6/2017 | Hautvast et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0251988 A1 | 9/2017 | Weber et al. |
| 2017/0280978 A1 | 10/2017 | Yamamoto |
| 2017/0281049 A1 | 10/2017 | Yamamoto |
| 2017/0290631 A1 | 10/2017 | Lee et al. |
| 2017/0304015 A1 | 10/2017 | Tavallaei et al. |
| 2017/0325715 A1 | 11/2017 | Mehendale et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |

FOREIGN PATENT DOCUMENTS

| | | |
|---|---|---|
| EP | 1 800 593 | 6/2007 |
| EP | 2 158 834 | 3/2010 |
| EP | 2 392 435 | 12/2011 |
| EP | 3 025 630 | 6/2016 |
| WO | WO 01/56457 | 8/2001 |
| WO | WO 06/122061 | 11/2006 |
| WO | WO 09/120940 | 10/2009 |
| WO | WO 11/132409 | 10/2011 |

OTHER PUBLICATIONS

Verdaasdonk et al., Jan. 23, 2012, Effect of microsecond pulse length and tip shape on explosive bubble formation of 2.78 μm Er,Cr;YSGG and 2.94 μm Er:YagAG laser, Proceedings of SPIE, vol. 8221, 12.

* cited by examiner

700

Receive a sample of images captured by an image sensor of an endoscope.
710

Generate a difference array for a pair of images of the sample.
720

Generate a gradient array for the pair of images of the sample.
730

Apply weights to the difference array and the gradient array.
740

Generate a set of calibration parameters based on the difference array and the gradient array.
750

FIG. 7

AUTOMATED ENDOSCOPE CALIBRATION

CROSS-REFERENCE TO RELATED APPLICATIONS

This application claims the benefit of and priority to U.S. Provisional Application No. 62/185,135 filed Jun. 26, 2015, which is incorporated by reference herein in its entirety. The subject matter of the present application is related to U.S. application Ser. No. 14/523,760, filed on Oct. 24, 2014, entitled "SYSTEM FOR ROBOTIC-ASSISTED ENDOLUMENAL SURGERY AND RELATED METHODS", the entire disclosure of which is incorporated herein by reference.

BACKGROUND

1. Field of Art

This description generally relates to surgical robotics, and particularly to an automated process for calibrating endoscopes.

2. Description of the Related Art

Robotic technologies have a range of applications. In particular, robotic arms help complete tasks that a human would normally perform. For example, factories use robotic arms to manufacture automobiles and consumer electronics products. Additionally, scientific facilities use robotic arms to automate laboratory procedures such as transporting microplates. Recently, physicians have started using robotic arms to help perform surgical procedures. For instance, physicians use robotic arms to control surgical instruments such as endoscopes.

Endoscopes with movable tips help perform surgical procedures in a minimally invasive manner. A movable tip can be directed to a remote location of a patient, such as the lung or blood vessel. Deviation of the tip's actual position from a target position may result in additional manipulation to correct the tip's position. Incorporating real time feedback of endoscope motions is difficult, for example, because endoscope tips are compressible and have a hysteresis. Further, existing techniques for manual calibration may rely on limited amounts of endoscope tip deflection that does not accurately model motions of the tip.

SUMMARY

A surgical robotic system automatically calibrates tubular and flexible surgical tools such as endoscopes. Surgical tools may exhibit nonlinear behavior, for example, due to friction and stiffness of the tool's material. By accounting for nonlinear behavior of an endoscope, the surgical robotic system can accurately model motions of the endoscope and navigate the endoscope while performing a surgical procedure on a patient. The surgical robotic system models the nonlinear behavior and movements using sets of calibration parameters determined based on images captured by an image sensor of the endoscope.

Calibration parameters can be determined using an image registration process. Changes between two of the captured images correspond to a shift in perspective of the image sensor due to a movement of the endoscope. For instance, the endoscope moves along a trajectory inside a calibration structure while capturing images of the surface of the calibration structure. The surgical robotic system calculates difference arrays and gradient arrays based on processing the captured images. Calibration parameters based on the arrays describe translational or rotational movements of the endoscope in one or more axis, e.g., pitch and yaw.

Calibration parameters can also be determined using calibration curves. The surgical robotic system generates the calibration curves based on position and orientation information of the endoscope captured by sensors. Calibration parameters based on the calibration curves describe a slope, hysteresis, or a dead zone value corresponding to the endoscope's movement in one or more axis.

In some embodiments, an endoscope includes tubular components referred to as a sheath and leader. The surgical robotic system moves the sheath and leader using an instrument device manipulator (IDM). For example, the IDM actuates pull wires coupled to the sheath or the leader, which causes the endoscope to articulate along different axis. The pull wires may also exhibit nonlinear behavior that can be modeled using the calibration parameters. The sheath and leader may include a helix section to mitigate unwanted bending and torqueing forces in the endoscope.

BRIEF DESCRIPTION OF DRAWINGS

FIG. 7 is a flowchart of a process that may be performed as part of the process illustrated in FIG. 8 to determine the movements of the endoscope from a sequence of recorded images according to one embodiment.

The figures depict embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

The methods and apparatus disclosed herein are well suited for use with one or more endoscope components or steps as described in U.S. application Ser. No. 14/523,760, filed on Oct. 24, 2014, published as U.S. Pat. Pub. No. US 2015/0119637, entitled "SYSTEM FOR ROBOTIC-ASSISTED ENDOLUMENAL SURGERY AND RELATED METHODS," the full disclosure of which has been previously incorporated by reference. The aforementioned application describes system components, endolumenal systems, virtual rail configurations, mechanism changer interfaces, instrument device manipulators (IDMs), endoscope tool designs, control consoles, endoscopes, instrument device manipulators, endolumenal navigation, and endolumenal procedures suitable for combination in accordance with embodiments disclosed herein.

I. Surgical Robotic System

Figure 1:
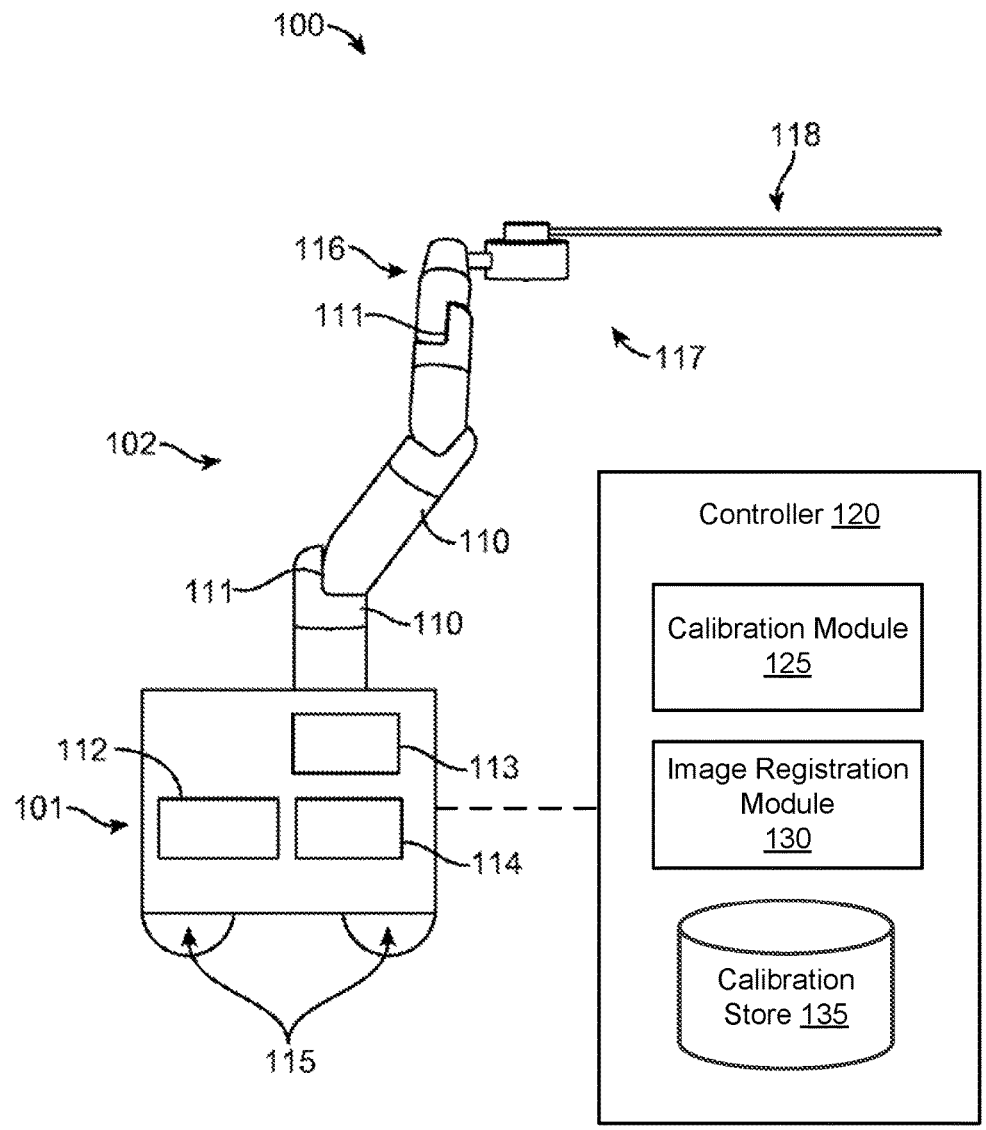
FIG. 1 illustrates a surgical robotic system according to one embodiment.

FIG. 1 illustrates a surgical robotic system 100 according to one embodiment. The surgical robotic system 100 includes a base 101 coupled to one or more robotic arms, e.g., robotic arm 102. The base 101 is communicatively coupled to a command console, which is further described with reference to FIG. 2 in Section II. Command Console.

The base 101 can be positioned such that the robotic arm 102 has access to perform a surgical procedure on a patient, while a user such as a physician may control the surgical robotic system 100 from the comfort of the command console. In some embodiments, the base 101 may be coupled to a surgical operating table or bed for supporting the patient. Though not shown in FIG. 1 for purposes of clarity, the base 101 may include subsystems such as control electronics, pneumatics, power sources, optical sources, and the like. The robotic arm 102 includes multiple arm segments 110 coupled at joints 111, which provides the robotic arm 102 multiple degrees of freedom, e.g., seven degrees of freedom corresponding to seven arm segments. The base 101 may contain a source of power 112, pneumatic pressure 113, and control and sensor electronics 114—including components such as a central processing unit, data bus, control circuitry, and memory—and related actuators such as motors to move the robotic arm 102. The electronics 114 in the base 101 may also process and transmit control signals communicated from the command console.

In some embodiments, the base 101 includes wheels 115 to transport the surgical robotic system 100. Mobility of the surgical robotic system 100 helps accommodate space constraints in a surgical operating room as well as facilitate appropriate positioning and movement of surgical equipment. Further, the mobility allows the robotic arms 102 to be configured such that the robotic arms 102 do not interfere with the patient, physician, anesthesiologist, or any other equipment. During procedures, a user may control the robotic arms 102 using control devices such as the command console.

In some embodiments, the robotic arm 102 includes set up joints that use a combination of brakes and counter-balances to maintain a position of the robotic arm 102. The counter-balances may include gas springs or coil springs. The brakes, e.g., fail safe brakes, may be include mechanical and/or electrical components. Further, the robotic arms 102 may be gravity-assisted passive support type robotic arms.

Each robotic arm 102 may be coupled to an instrument device manipulator (IDM) 117 using a mechanism changer interface (MCI) 116. The IDM 117 can be removed and replaced with a different type of IDM, for example, a first type of IDM manipulates an endoscope, while a second type of IDM manipulates a laparoscope. The MCI 116 includes connectors to transfer pneumatic pressure, electrical power, electrical signals, and optical signals from the robotic arm 102 to the IDM 117. The MCI 116 can be a set screw or base plate connector. The IDM 117 manipulates surgical instruments such as the endoscope 118 using techniques including direct drive, harmonic drive, geared drives, belts and pulleys, magnetic drives, and the like. The MCI 116 is interchangeable based on the type of IDM 117 and can be customized for a certain type of surgical procedure. The robotic 102 arm can include a joint level torque sensing and a wrist at a distal end, such as the KUKA AG® LBR5 robotic arm.

The endoscope 118 is a tubular and flexible surgical instrument that is inserted into the anatomy of a patient to capture images of the anatomy (e.g., body tissue). In particular, the endoscope 118 includes one or more imaging devices (e.g., cameras or sensors) that capture the images. The imaging devices may include one or more optical components such as an optical fiber, fiber array, or lens. The optical components move along with the tip of the endoscope 118 such that movement of the tip of the endoscope 118 results in changes to the images captured by the imaging devices. The endoscope 118 is further described with reference to FIGS. 3A-I in Section III. Endoscope.

Robotic arms 102 of the surgical robotic system 100 manipulate the endoscope 118 using elongate movement members. The elongate movement members may include pull wires, also referred to as pull or push wires, cables, fibers, or flexible shafts. For example, the robotic arms 102 actuate multiple pull wires coupled to the endoscope 118 to deflect the tip of the endoscope 118. The pull wires may include both metallic and non-metallic materials such as stainless steel, Kevlar, tungsten, carbon fiber, and the like. The endoscope 118 may exhibit nonlinear behavior in response to forces applied by the elongate movement members. The nonlinear behavior may be based on stiffness and compressibility of the endoscope 118, as well as variability in slack or stiffness between different elongate movement members.

The surgical robotic system 100 includes a controller 120, for example, a computer processor. The controller 120 includes a calibration module 125, image registration module 130, and a calibration store 135. The calibration module 125 can characterize the nonlinear behavior using a model with piecewise linear responses along with parameters such as slopes, hystereses, and dead zone values. The calibration module 125 and calibration store 135 are further described in Sections IV-V: Calibration Dome and Calibration Curves. The surgical robotic system 100 can more accurately control an endoscope 118 by determining accurate values of the parameters. The surgical robotic system 100 also uses the image registration module 130 for calibration, which is further described in Section VI. Image Registration. In some embodiments, some or all functionality of the controller 120 is performed outside the surgical robotic system 100, for example, on another computer system or server communicatively coupled to the surgical robotic system 100.

II. Command Console

Figure 2:
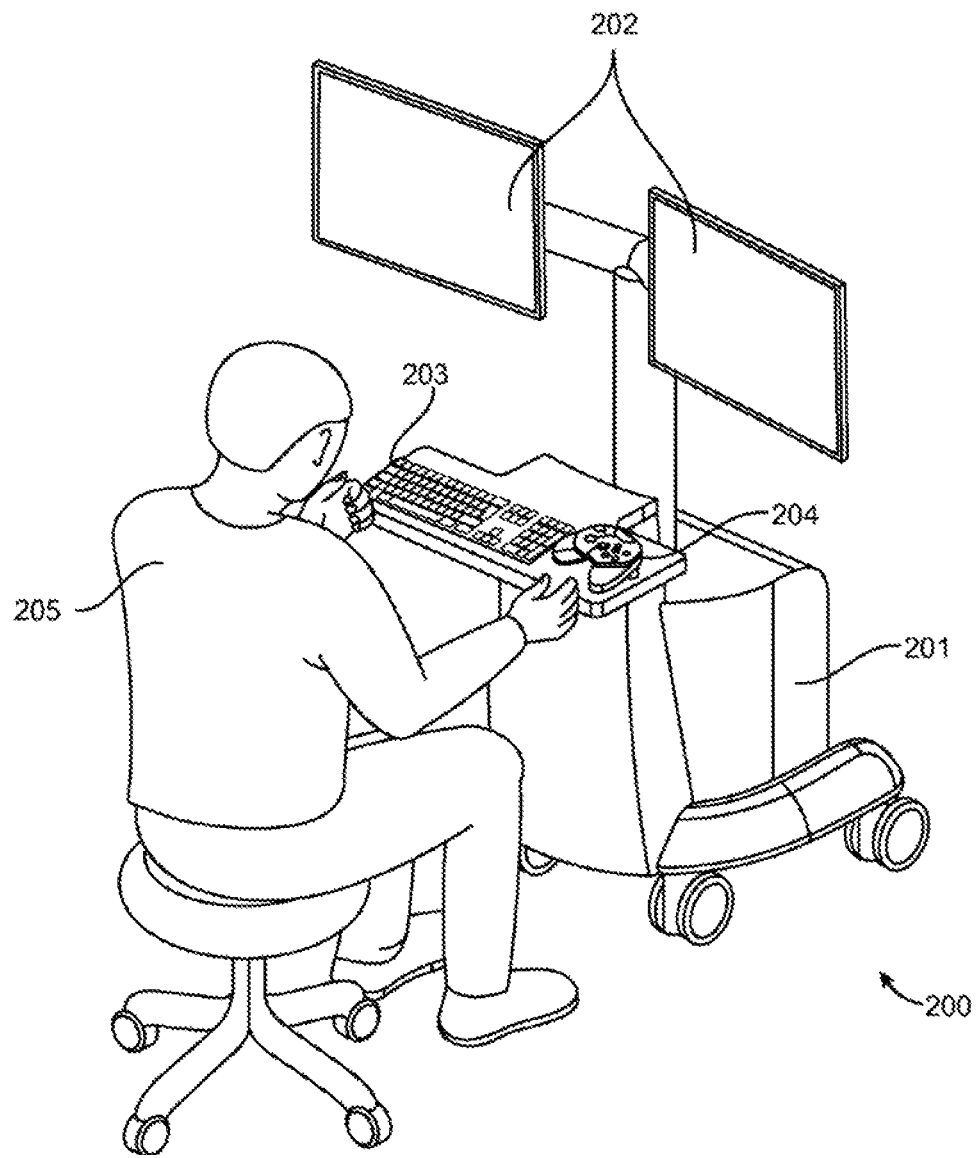
FIG. 2 illustrates a command console for a surgical robotic system according to one embodiment.

FIG. 2 illustrates a command console 200 for a surgical robotic system 100 according to one embodiment. The command console 200 includes a console base 201, display modules 202, e.g., monitors, and control modules, e.g., a keyboard 203 and joystick 204. In some embodiments, one or more of the command module 200 functionality may be integrated into a base 101 of the surgical robotic system 100 or another system communicatively coupled to the surgical robotic system 100. A user 205, e.g., a physician, remotely controls the surgical robotic system 100 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 118 shown in FIG. 1. In some embodiments, both the console base 201 and the base 101 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, trackpads, trackballs, control pads, video game controllers, and sensors (e.g., motion sensors or cameras) that capture hand gestures and finger gestures.

The user 205 can control a surgical instrument such as the endoscope 118 using the command console 200 in a velocity mode or position control mode. In velocity mode, the user 205 directly controls pitch and yaw motion of a distal end of the endoscope 118 based on direct manual control using the control modules. For example, movement on the joystick 204 may be mapped to yaw and pitch movement in the distal end of the endoscope 118. The joystick 204 can provide haptic feedback to the user 205. For example, the joystick 204 vibrates to indicate that the endoscope 118 cannot further translate or rotate in a certain direction. The command console 200 can also provide visual feedback (e.g., pop-up messages) and/or audio feedback (e.g., beeping) to indicate that the endoscope 118 has reached maximum translation or rotation.

In position control mode, the command console 200 uses a three-dimensional (3D) map of a patient and pre-determined computer models of the patient to control a surgical instrument, e.g., the endoscope 118. The command console 200 provides control signals to robotic arms 102 of the surgical robotic system 100 to manipulate the endoscope 118 to a target location. Due to the reliance on the 3D map, position control mode requires accurate mapping of the anatomy of the patient.

In some embodiments, users 205 can manually manipulate robotic arms 102 of the surgical robotic system 100 without using the command console 200. During setup in a surgical operating room, the users 205 may move the robotic arms 102, endoscopes 118, and other surgical equipment to access a patient. The surgical robotic system 100 may rely on force feedback and inertia control from the users 205 to determine appropriate configuration of the robotic arms 102 and equipment.

The display modules 202 may include electronic monitors, virtual reality viewing devices, e.g., goggles or glasses, and/or other means of display devices. In some embodiments, the display modules 202 are integrated with the control modules, for example, as a tablet device with a touchscreen. Further, the user 205 can both view data and input commands to the surgical robotic system 100 using the integrated display modules 202 and control modules.

The display modules 202 can display 3D images using a stereoscopic device, e.g., a visor or goggle. The 3D images provide an "endo view" (i.e., endoscopic view), which is a computer 3D model illustrating the anatomy of a patient. The "endo view" provides a virtual environment of the patient's interior and an expected location of an endoscope 118 inside the patient. A user 205 compares the "endo view" model to actual images captured by a camera to help mentally orient and confirm that the endoscope 118 is in the correct—or approximately correct—location within the patient. The "endo view" provides information about anatomical structures, e.g., the shape of an intestine or colon of the patient, around the distal end of the endoscope 118. The display modules 202 can simultaneously display the 3D model and computerized tomography (CT) scans of the anatomy the around distal end of the endoscope 118. Further, the display modules 202 may overlay pre-determined optimal navigation paths of the endoscope 118 on the 3D model and CT scans.

In some embodiments, a model of the endoscope 118 is displayed with the 3D models to help indicate a status of a surgical procedure. For example, the CT scans identify a lesion in the anatomy where a biopsy may be necessary. During operation, the display modules 202 may show a reference image captured by the endoscope 118 corresponding to the current location of the endoscope 118. The display modules 202 may automatically display different views of the model of the endoscope 118 depending on user settings and a particular surgical procedure. For example, the display modules 202 show an overhead fluoroscopic view of the endoscope 118 during a navigation step as the endoscope 118 approaches an operative region of a patient.

III. Endoscope

Figure 3A:
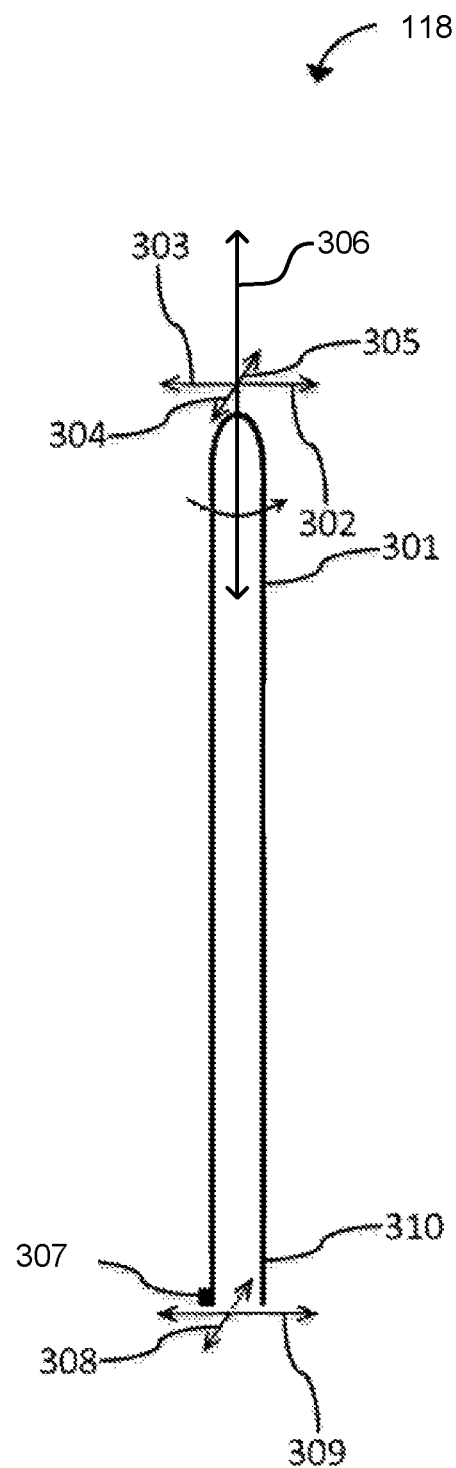
FIG. 3A illustrates multiple degrees of motion of an endoscope according to one embodiment.

FIG. 3A illustrates multiple degrees of motion of an endoscope 118 according to one embodiment. The endoscope 118 is an embodiment of the endoscope 118 shown in FIG. 1. As shown in FIG. 3A, the tip 301 of the endoscope 118 is oriented with zero deflection relative to a longitudinal axis 306 (also referred to as a roll axis 306). To capture images at different orientations of the tip 301, a surgical robotic system 100 deflects the tip 301 on a positive yaw axis 302, negative yaw axis 303, positive pitch axis 304, negative pitch axis 305, or roll axis 306. The tip 301 or body 310 of the endoscope 118 may be elongated or translated in the longitudinal axis 306, x-axis 308, or y-axis 309.

The endoscope 118 includes a reference structure 307 to calibrate the position of the endoscope 118. For example, the surgical robotic system 100 measures deflection of the endoscope 118 relative to the reference structure 307. The reference structure 307 is located on a proximal end of the endoscope 118 and may include a key, slot, or flange. The reference structure 307 is coupled to a first drive mechanism for calibration and coupled to a second drive mechanism, e.g., the IDM 117, to perform a surgical procedure. The calibration process of the endoscope is further described in Sections IV-VII. Calibration Dome, Calibration Curves, Image Registration, and Process Flows.

Figure 3B:
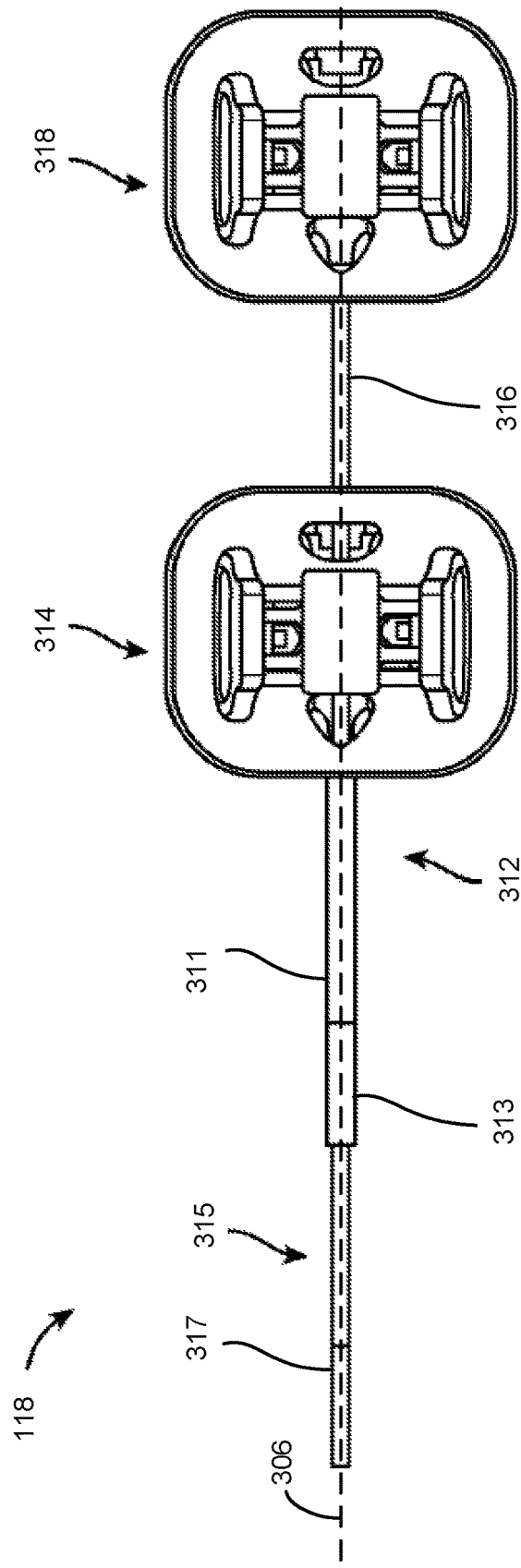
FIG. 3B is a top view of an endoscope according to one embodiment.

FIG. 3B is a top view of an endoscope 118 according to one embodiment. The endoscope 118 includes a leader 315 tubular component nested or partially nested inside and longitudinally-aligned with a sheath 311 tubular component. The sheath 311 includes a proximal sheath section 312 and distal sheath section 313. The leader 315 has a smaller outer diameter than the sheath 311 and includes a proximal leader section 316 and distal leader section 317. The sheath base 314 and the leader base 318 actuate the distal sheath section 313 and the distal leader section 317, respectively, for example, based on control signals from a user of a surgical robotic system 100. The sheath base 314 and the leader base 318 are, e.g., part of the IDM 117 shown in FIG. 1.

Both the sheath base 314 and the leader base 318 include drive mechanisms (e.g., the independent drive mechanism further described with reference to FIG. 4A-D in Section III. D. Instrument Device Manipulator) to control pull wires coupled to the sheath 311 and leader 315. For example, the sheath base 314 generates tensile loads on pull wires coupled to the sheath 311 to deflect the distal sheath section 313. Similarly, the leader base 318 generates tensile loads on pull wires coupled to the leader 315 to deflect the distal leader section 317. Both the sheath base 314 and leader base 318 may also include couplings for the routing of pneumatic pressure, electrical power, electrical signals, or optical signals from IDMs to the sheath 311 and leader 314, respectively. A pull wire may include a steel coil pipe along the length of the pull wire within the sheath 311 or the leader 315, which transfers axial compression back to the origin of the load, e.g., the sheath base 314 or the leader base 318, respectively.

The endoscope 118 can navigate the anatomy of a patient with ease due to the multiple degrees of freedom provided by pull wires coupled to the sheath 311 and the leader 315. For example, four or more pull wires may be used in either the sheath 311 and/or the leader 315, providing eight or more degrees of freedom. In other embodiments, up to three pull wires may be used, providing up to six degrees of freedom. The sheath 311 and leader 315 may be rotated up to 360 degrees along a longitudinal axis 306, providing more degrees of motion. The combination of rotational angles and multiple degrees of freedom provides a user of the surgical robotic system 100 with a user friendly and instinctive control of the endoscope 118.

III. A. Endoscope Sheath

Figure 3C:
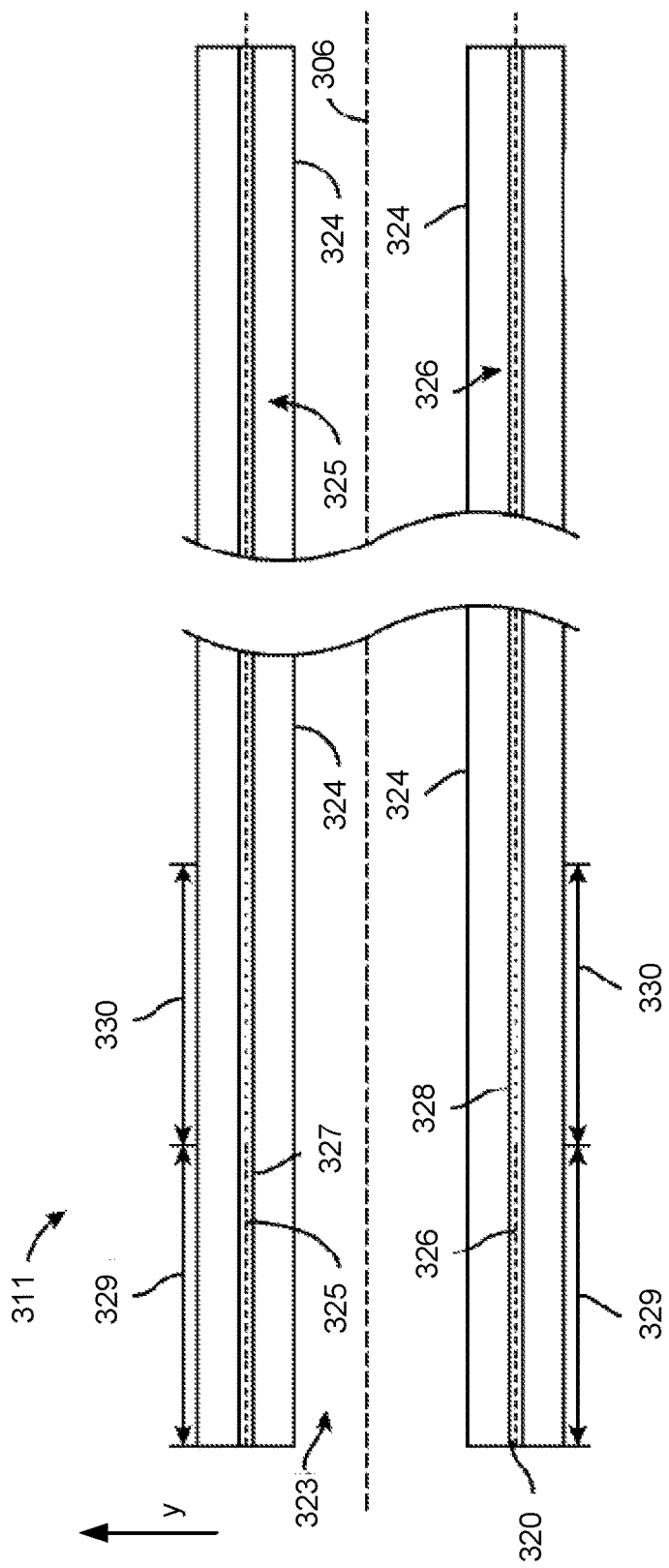
FIG. 3C is a cross sectional side view of a sheath of an endoscope according to one embodiment.

FIG. 3C is a cross sectional side view of the sheath 311 of the endoscope 118 according to one embodiment. The sheath 311 includes a lumen 323 sized to accommodate a tubular component such as the leader 315 shown in FIG. 3B. The sheath 311 includes walls 324 with pull wires 325 and 326 running through conduits 327 and 328 inside the length of walls 324. The conduits include a helix section 330 and a distal non-helix section 329. Appropriate tensioning of pull wire 325 may compress the distal end 320 in the positive y-axis direction, while minimizing bending of the helix section 330. Similarly, appropriate tensioning of pull wire 326 may compress distal end 320 in the negative y-axis direction. In some embodiments, the lumen 323 is not concentric with the sheath 311.

Pull wires 325 and 326 do not necessarily run straight through the length of sheath 311. Rather, the pull wires 325 and 326 spiral around sheath 311 along helix section 330 and run longitudinally straight (i.e., approximately parallel to the longitudinal axis 306) along the distal non-helix section 329 and any other non-helix section of the sheath 311. The helix section 330 may start and end anywhere along the length of the sheath 311. Further, the length and pitch of helix section 330 may be determined based on desired properties of sheath 311, e.g., flexibility of the sheath 311 and friction in the helix section 330.

Though the pull wires 325 and 326 are positioned at 180 degrees relative to each other in FIG. 3C, it should be noted that pull wires of the sheath 311 may be positioned at different angles. For example, three pull wires of a sheath may each be positioned at 120 degrees relative to each other. In some embodiments, the pull wires are not equally spaced relative to each other, i.e., without a constant angle offset.

III. B. Helix Sections

Figure 3D:
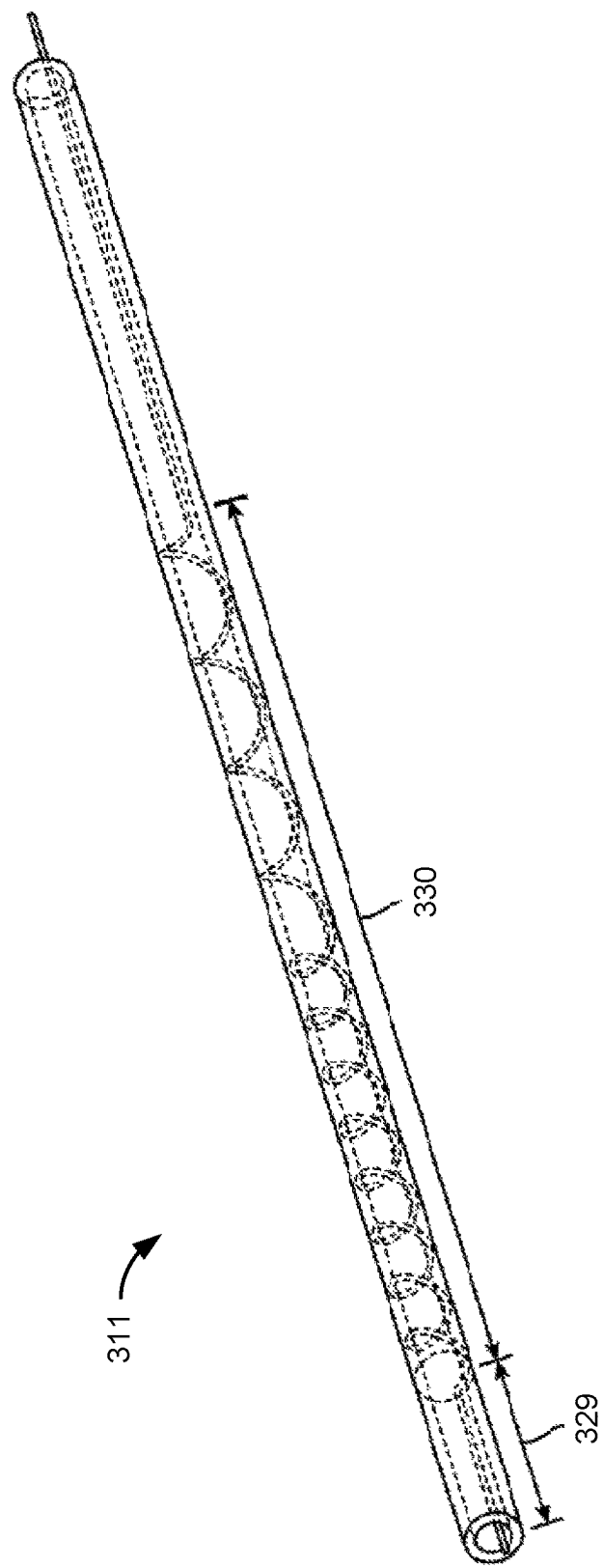
FIG. 3D is an isometric view of a helix section of a sheath of an endoscope according to one embodiment.

FIG. 3D is an isometric view of a helix section 330 of the sheath 311 of the endoscope 118 according to one embodiment. FIG. 3D shows only one pull wire for the purpose of distinguishing between the distal non-helix section 329 and the helix section 330. In some embodiments, the helix section 330 has a variable pitch.

Figure 3E:
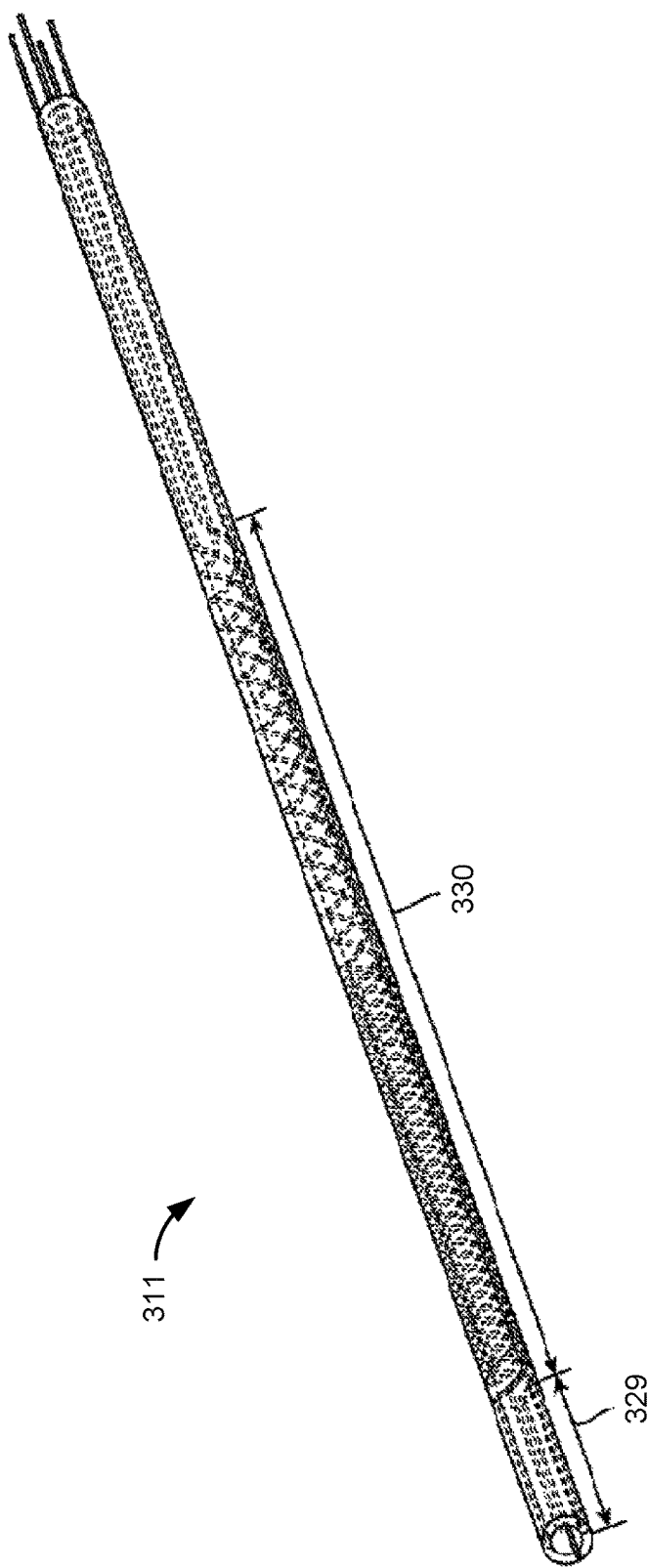
FIG. 3E is another isometric view of a helix section of a sheath of an endoscope according to one embodiment.

FIG. 3E is another isometric view of a helix section 330 of a sheath 311 of an endoscope 118 according to one embodiment. FIG. 3E shows four pull wires extending along the distal non-helix section 329 and the variable pitch helix section 330.

Helix sections 330 in the sheath 311 and leader 315 of the endoscope 118 help a surgical robotic system 100 and/or a user navigate the endoscope 118 through nonlinear pathways in the anatomy of a patient, e.g., intestines or the colon. When navigating the nonlinear pathways, it is useful for the endoscope 118 to remain flexible, while still having a controllable distal section (in both the sheath 311 and the leader 315). Further, it is advantageous to reduce the amount of unwanted bending along the endoscope 118. In previous endoscope designs, tensioning the pull wires to manipulate the distal section generated the unwanted bending and torqueing along a length of the endoscope, which may be referred to as muscling and curve alignment, respectively.

Figures 3F, 3G:
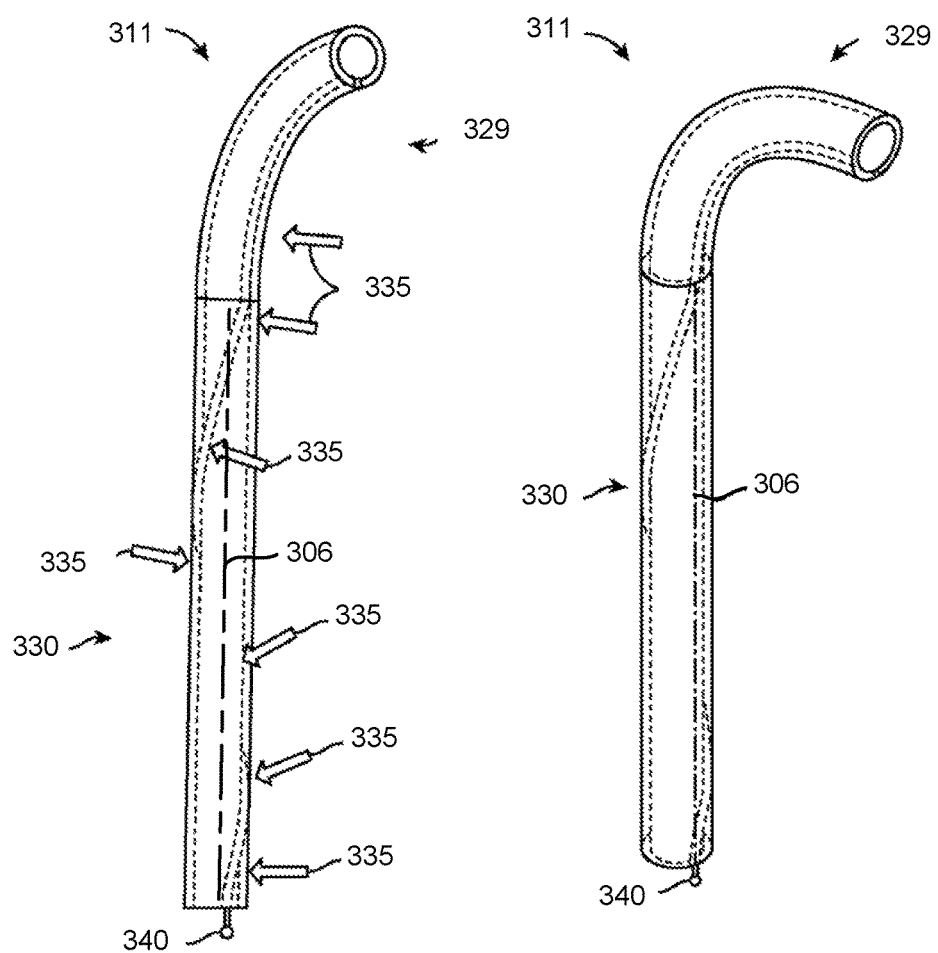
FIG. 3F is a side view of a sheath of an endoscope with a helix section according to one embodiment.
FIG. 3G is another view of the sheath of the endoscope shown in FIG. 3F according to one embodiment.

FIG. 3F is a side view of the sheath 311 of the endoscope 118 with a helix section 330 according to one embodiment. FIGS. 3F-G illustrate how the helix section 330 helps substantially mitigate muscling and curve alignment. Since the pull wire 340 is spiraled around the length of helix section 330, the pull wire 340 radially and symmetrically distributes a compressive load 335 in multiple directions around the longitudinal axis 306. Further, bending moments imposed on the endoscope 118 are also symmetrically distributed around the longitudinal axis 306, which counterbalances and offsets opposing compressive forces and tensile forces. The distribution of the bending moments results in minimal net bending and rotational forces, creating a low potential energy state of the endoscope 118, and thus eliminating or substantially mitigating muscling and curve alignment.

The pitch of the helix section 330 can affect the friction and the stiffness of the helix section 330. For example, the helix section 330 may be shorter to allow for a longer distal non-helix section 329, resulting in less friction and/or stiffness of the helix section 330.

FIG. 3G is another view of the sheath 311 of the endoscope 118 shown in FIG. 3F according to one embodiment. Compared to the distal non-helix section 329 shown in FIG. 3F, the distal non-helix section 329 shown in FIG. 3G is deflected at a greater angle.

III. C. Endoscope Leader

Figure 3H:
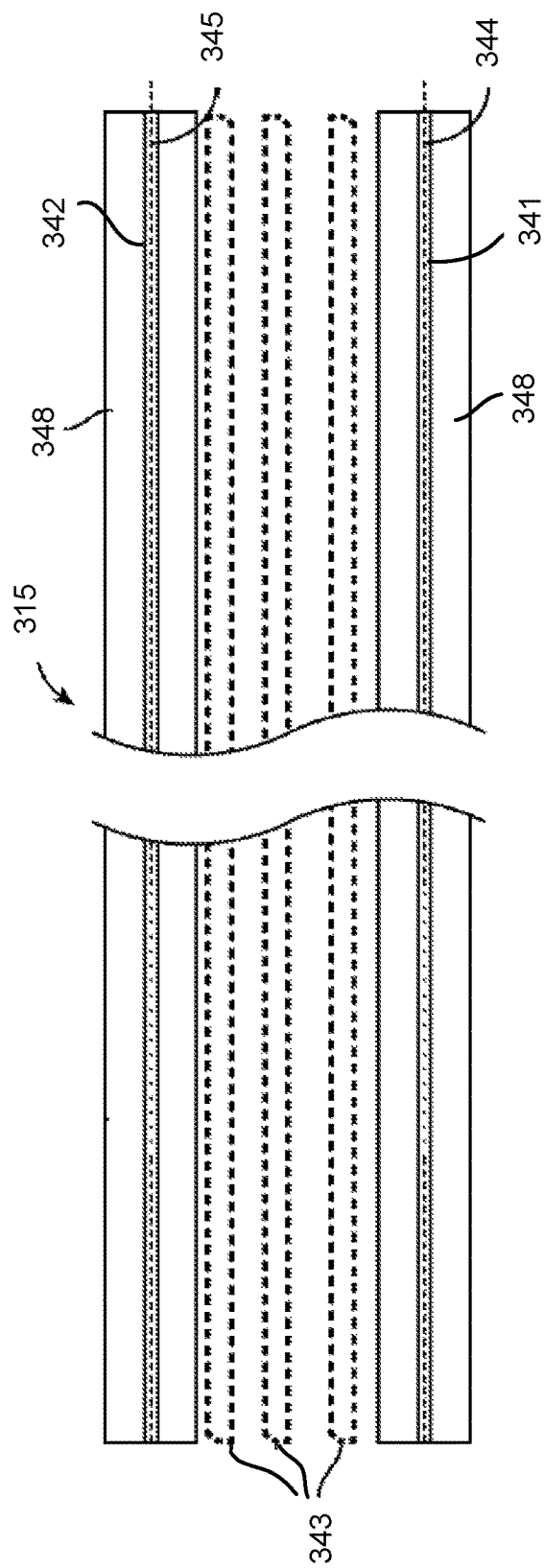
FIG. 3H is a cross sectional side view of a leader of an endoscope according to one embodiment.

FIG. 3H is a cross sectional side view of the leader 315 of the endoscope 118 according to one embodiment. The leader 315 includes at least one working channel 343 and pull wires 344 and 345 running through conduits 341 and 342, respectively, along the length of the walls 348. The pull wires 344 and 345 and conduits 341 and 342 are substantially the same as the pull wires 325 and 326 and the conduits 327 and 328 in FIG. 3C, respectively. For example, the pull wires 344 and 345 may have a helix section that helps mitigate muscling and curve alignment of the leader 315, similar to the sheath 311 as previously described.

Figure 3I:
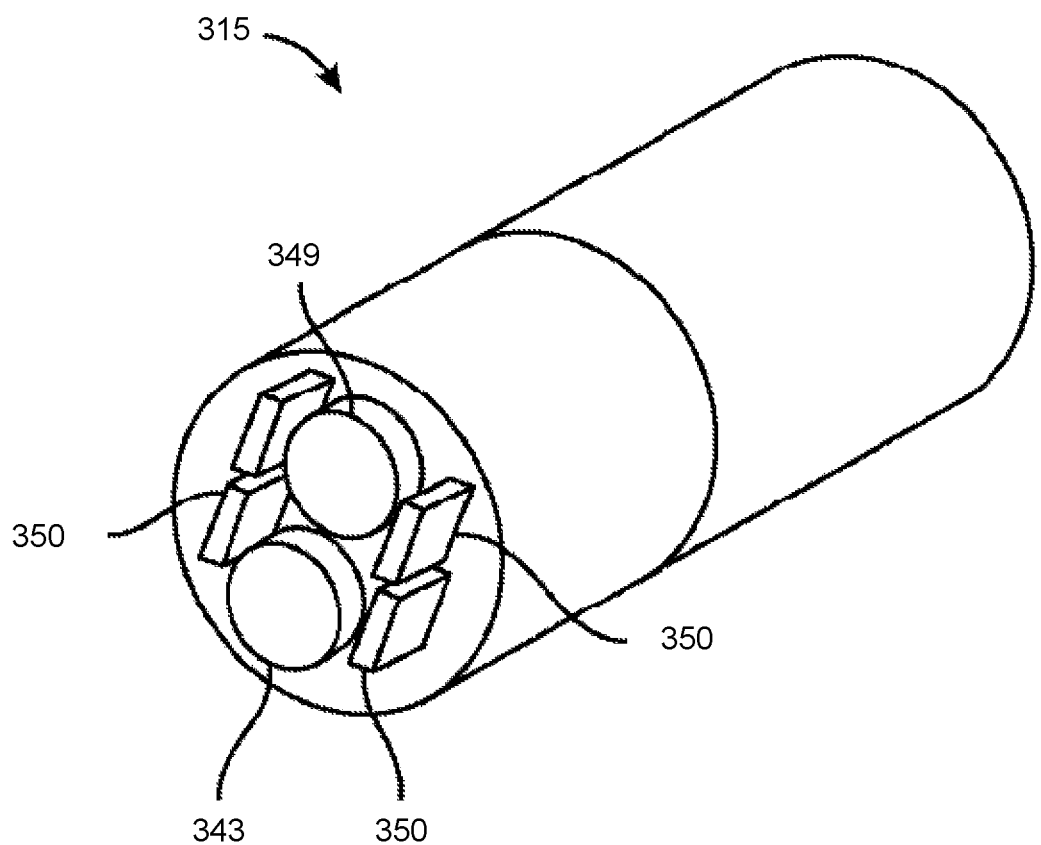
FIG. 3I is a cross sectional isometric view of the leader of the endoscope shown in FIG. 3H according to one embodiment.

FIG. 3I is a cross sectional isometric view of the leader 315 of the endoscope 118 shown in FIG. 3H according to one embodiment. The leader 315 includes an imaging device 349 (e.g., charge-coupled device (CCD) or complementary metal-oxide semiconductor (CMOS) camera, imaging fiber bundle, etc.), light sources 350 (e.g., light-emitting diode (LED), optic fiber, etc.), and at least one working channel 343 for other components. For example, other components include camera wires, an insufflation device, a suction device, electrical wires, fiber optics, an ultrasound transducer, electromagnetic (EM) sensing components, and optical coherence tomography (OCT) sensing components. In some embodiments, the leader 315 includes a pocket hole to accommodate insertion of a component into a working channel 343.

III. D. Instrument Device Manipulator

Figure 4A:
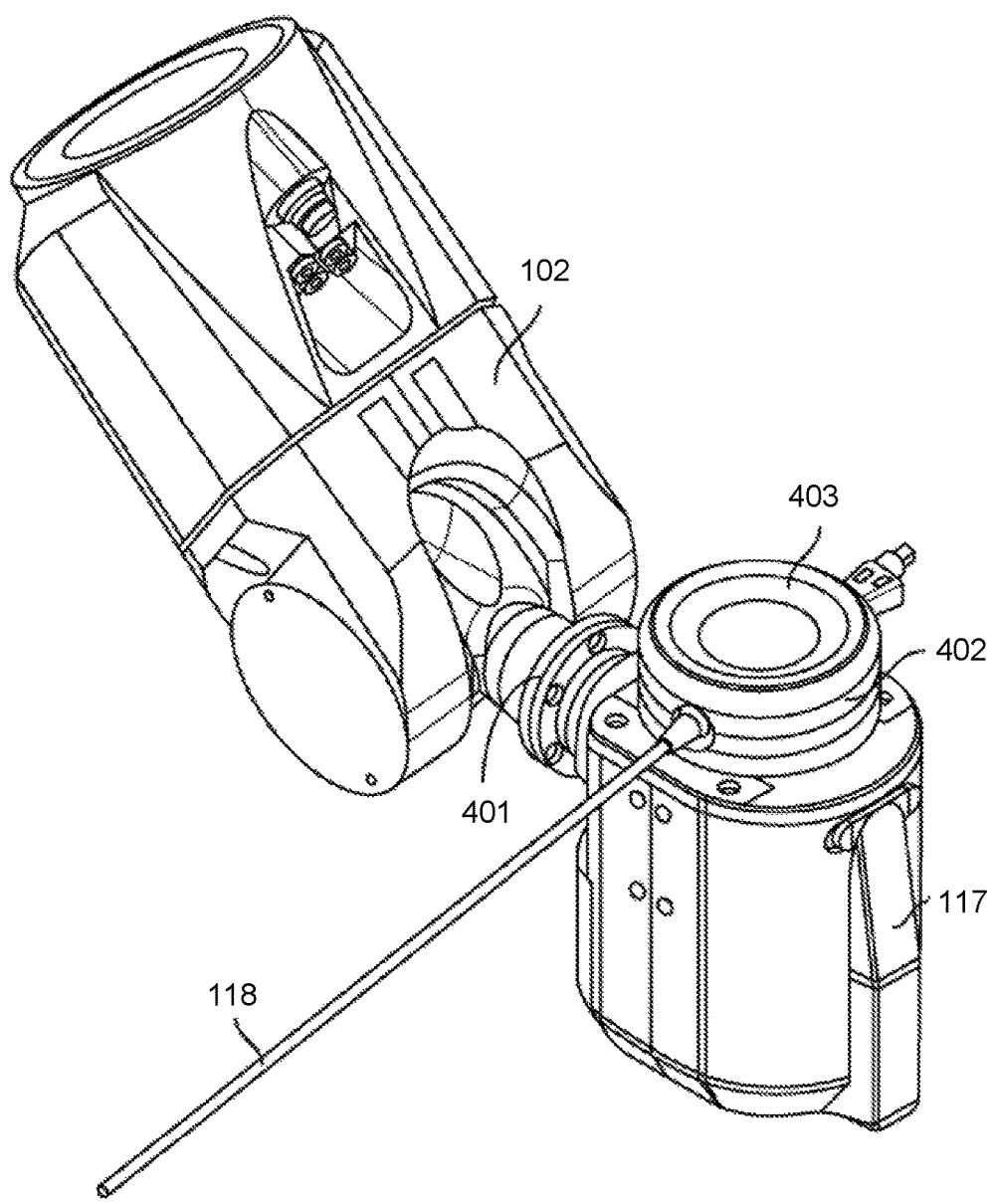
FIG. 4A is an isometric view of an instrument device manipulator of a surgical robotic system according to one embodiment.

FIG. 4A is an isometric view of an instrument device manipulator 117 of the surgical robotic system 100 according to one embodiment. The robotic arm 102 is coupled to the IDM 117 via an articulating interface 401. The IDM 117 is coupled to the endoscope 118. The articulating interface 401 may transfer pneumatic pressure, power signals, control signals, and feedback signals to and from the robotic arm 102 and the IDM 117. The IDM 117 may include a gear head, motor, rotary encoder, power circuits, and control circuits. A tool base 403 for receiving control signals from the IDM 117 is coupled to the proximal end of the endoscope 118. Based on the control signals, the IDM 117 manipulates the endoscope 118 by actuating output shafts, which are further described below with reference to FIG. 4B.

Figure 4B:
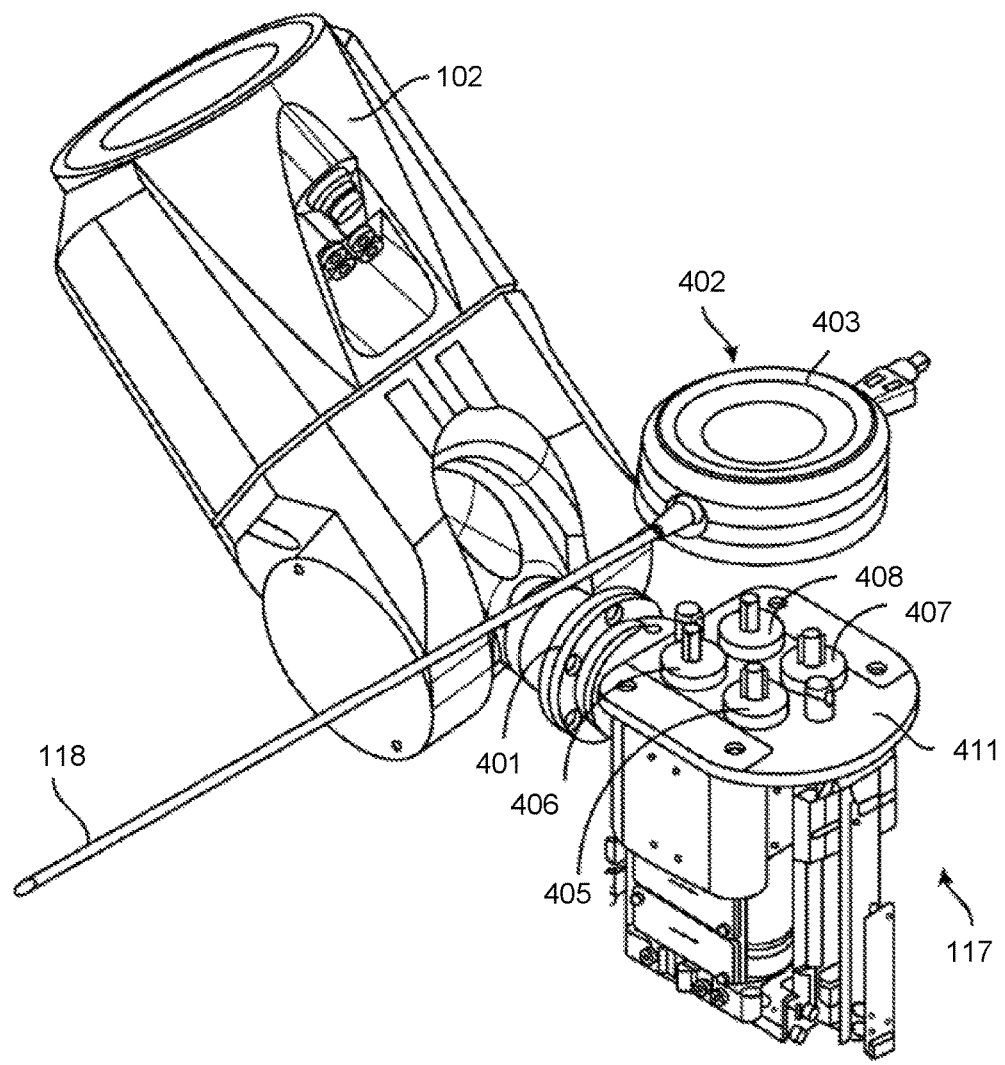
FIG. 4B is an exploded isometric view of the instrument device manipulator shown in FIG. 4A according to one embodiment.

FIG. 4B is an exploded isometric view of the instrument device manipulator shown in FIG. 4A according to one embodiment. In FIG. 4B, the endoscopic 118 has been removed from the IDM 117 to reveal the output shafts 405, 406, 407, and 408.

Figure 4C:
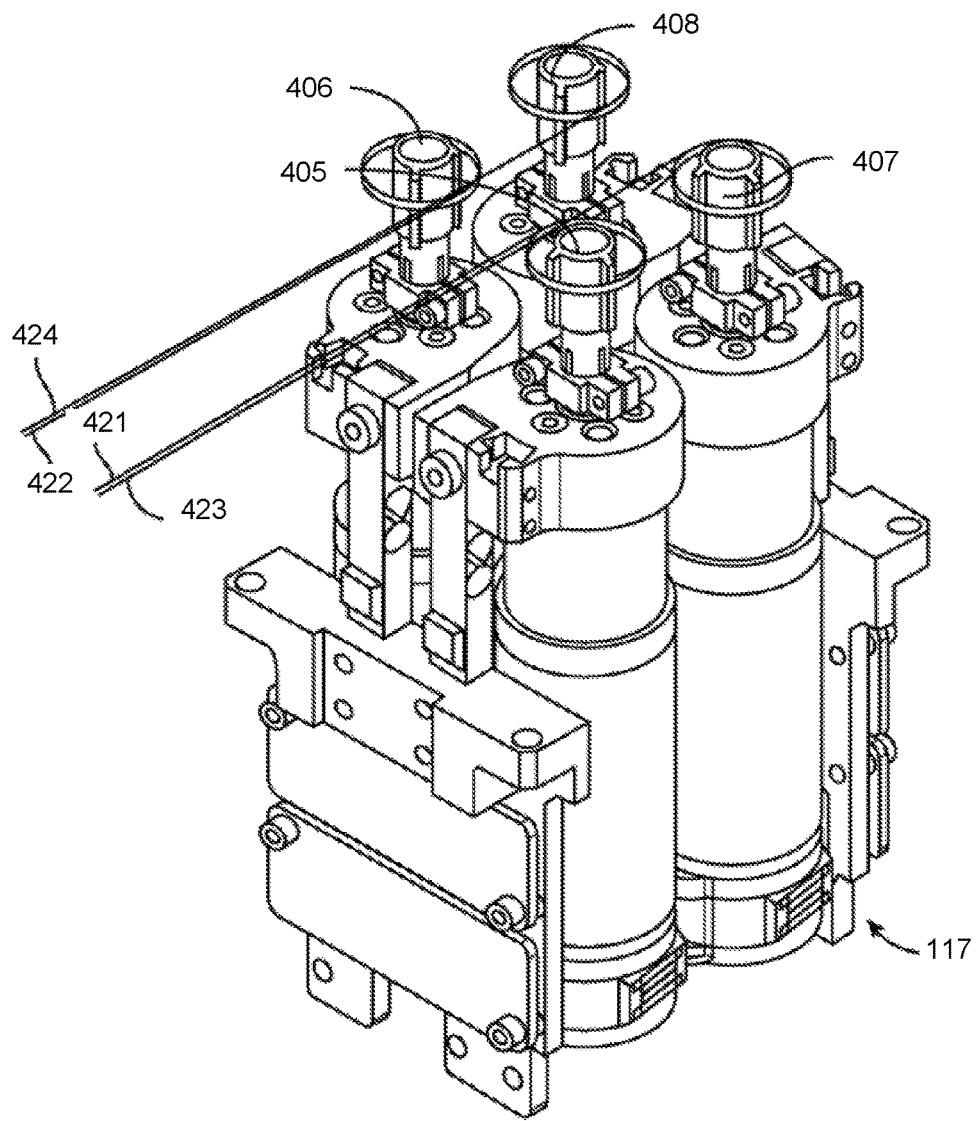
FIG. 4C is an isometric view of an independent drive mechanism of the instrument device manipulator shown in FIG. 4A according to one embodiment.

FIG. 4C is an isometric view of an independent drive mechanism of the instrument device manipulator 117 shown in FIG. 4A according to one embodiment. The independent drive mechanism can tighten or loosen the pull wires 421, 422, 423, and 424 (e.g., independently from each other) of an endoscope by rotating the output shafts 405, 406, 407, and 408 of the IDM 117, respectively. Just as the output shafts 405, 406, 407, and 408 transfer force down pull wires 421, 422, 423, and 424, respectively, through angular motion, the pull wires 421, 422, 423, and 424 transfer force back to the output shafts. The IDM 117 and/or the surgical robotic system 100 can measure the transferred force using a sensor, e.g., a strain gauge further described below.

Figure 4D:
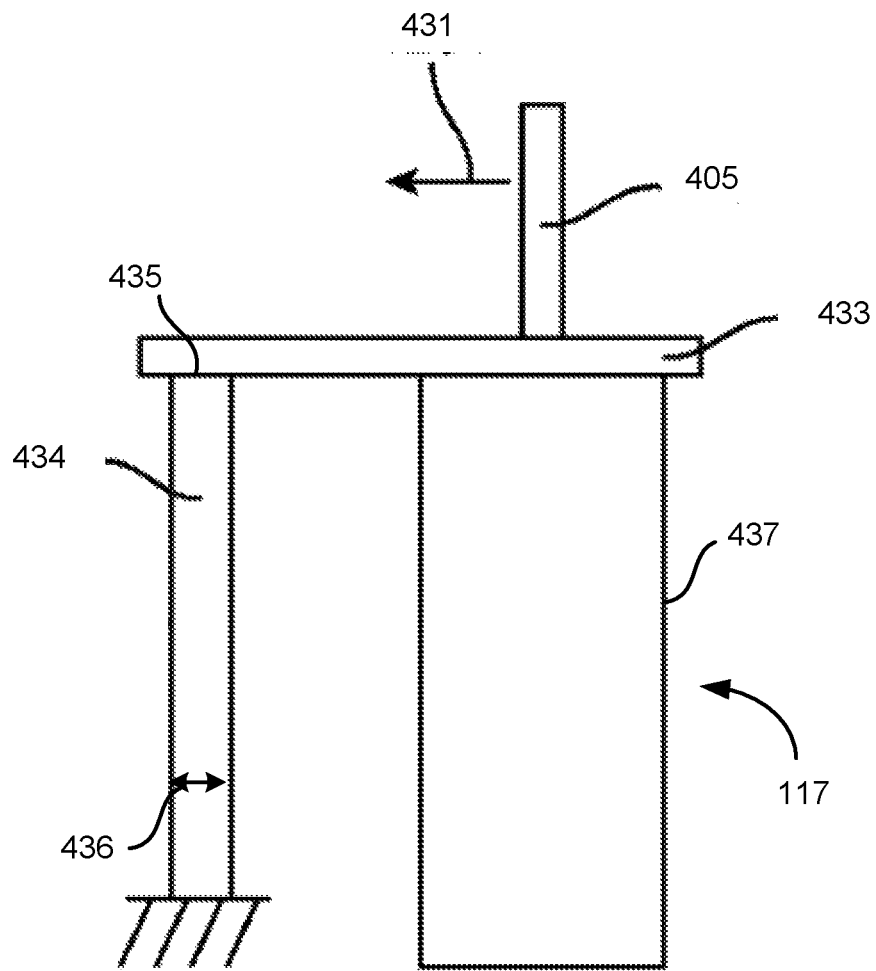
FIG. 4D illustrates a conceptual diagram that shows how forces may be measured by a strain gauge of the independent drive mechanism shown in FIG. 4C according to one embodiment.

FIG. 4D illustrates a conceptual diagram that shows how forces may be measured by a strain gauge 434 of the independent drive mechanism shown in FIG. 4C according to one embodiment. A force 431 may directed away from the output shaft 405 coupled to the motor mount 433 of the motor 437. Accordingly, the force 431 results in horizontal displacement of the motor mount 433. Further, the strain gauge 434 horizontally coupled to the motor mount 433 experiences strain in the direction of the force 431. The strain may be measured as a ratio of the horizontal displacement of the tip 435 of strain gauge 434 to the overall horizontal width 436 of the strain gauge 434.

In some embodiments, the IDM 117 includes additional sensors, e.g., inclinometers or accelerometers, to determine an orientation of the IDM 117. Based on measurements from the additional sensors and/or the strain gauge 434, the surgical robotic system 100 can calibrate readings from the strain gauge 434 to account for gravitational load effects. For example, if the IDM 117 is oriented on a horizontal side of the IDM 117, the weight of certain components of the IDM 117 may cause a strain on the motor mount 433. Accordingly, without accounting for gravitational load effects, the strain gauge 434 may measure strain that did not result from strain on the output shafts.

IV. Calibration Dome

During calibration of the endoscope 118, the surgical robotic system 100 measures calibration parameters. The calibration parameters may describe a movement of the endoscope 118 (e.g., translational or rotational); a hysteresis in pitch or yaw of the endoscope 118; a stiffness in pitch, yaw, or along the length of the endoscope 118; a compression in pitch or yaw of the endoscope 118; a positive or negative pitch angle of the endoscope 118; a positive or negative yaw angle of the endoscope 118; a roll angle of the endoscope 118; and/or a working length between a mechanism (e.g., the reference structure 307) coupled to the proximal end and the distal end of the endoscope 118. The endoscope 118 may include a computer readable tangible medium, e.g., flash memory, to store the calibration parameters. In some embodiments, the calibration parameters are stored with a unique identifier of the endoscope 118. The surgical robotic system 100, via the calibration module 125, can also store the calibration parameters in the calibration store 135 and/or upload the calibration parameters and the unique identifier to a global calibration database including information from multiple endoscopes.

The calibration parameters may vary between different endoscopes. For example, in response to the same command, one endoscope tip rotates 10 degrees in pitch while another endoscope rotates 20 degrees in pitch and 1 degree in yaw. Thus, the calibration parameters to compensate for nonlinearities of the responses of the two endoscopes will differ in value. The calibration parameters can be determined for the sheath and/or leader of an endoscope. In some embodiments, the calibration parameters for the sheath are different than the calibration parameters for the leader, e.g., because the sheath and leader have different helix sections. The embodiments disclosed herein provide a method and apparatus for accurately and continuously measuring the endoscope's motion during a calibration process, for example by measuring a trajectory of the endoscope during calibration. The calibration process is automated using the surgical robotic system 100. Although reference is made to calibration with imaging, the surgical robotic system 100 may perform calibration using other data collection methods, e.g., using magnetic field sensors and accelerometers.

Figure 5A:
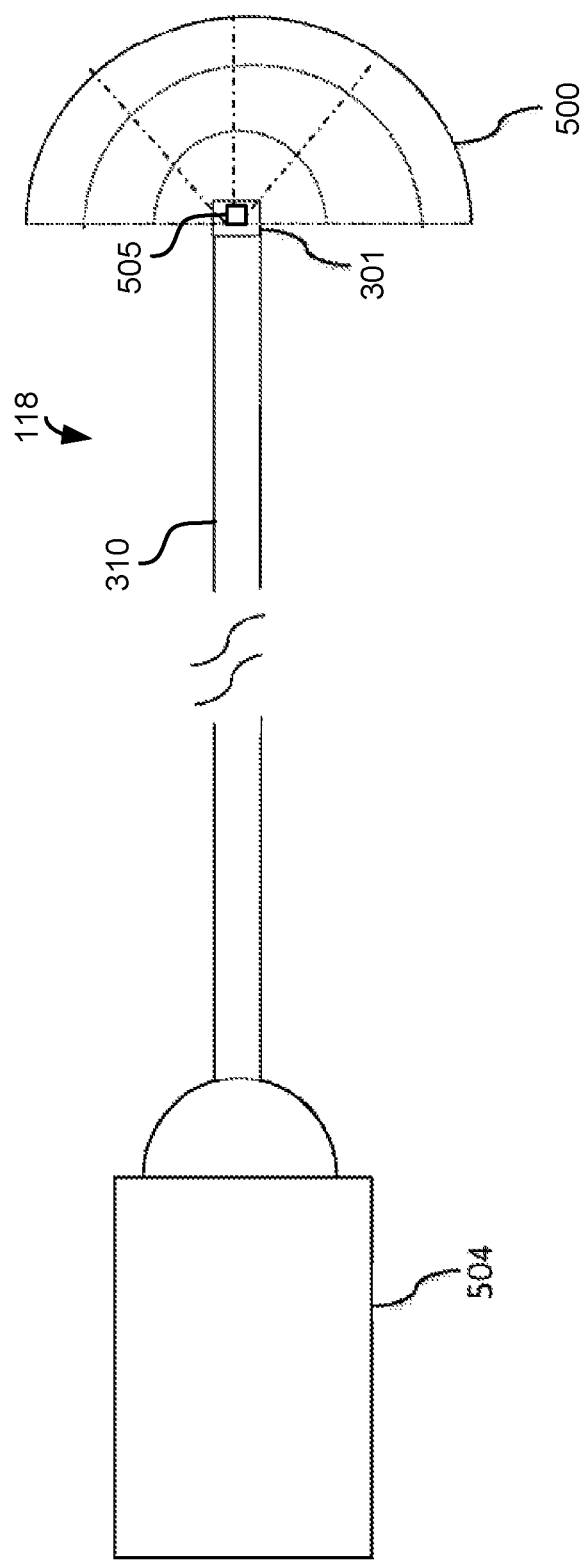
FIG. 5A illustrates an example calibration setup for a robotically-controlled endoscope according to one embodiment.

FIG. 5A illustrates an example calibration setup for a robotically-controlled endoscope 118 according to one embodiment. The endoscope 118 is oriented so that endoscope's tip 301 is secured within a calibration structure 500 with a visual pattern on a surface of the calibration structure 500 and visible to an image sensor 505, e.g., a camera, mounted on the tip 301. For example, the visual pattern includes checkered squares. A proximal end of the endoscope 118 is secured to the calibration structure 500 while the endoscope's body 310 and tip 301 can move around inside the calibration structure 500.

An actuation device 504, e.g., the IDM 117 shown in FIG. 1, is coupled to the endoscope 118 and may receive signals, e.g., from the command console 200 shown in FIG. 2. The signals may also be referred to as control signals or commands. Based on the signals, the actuation device 504 manipulates the endoscope 118 within the calibration structure 500. The signals may indicate an intended trajectory for the endoscope 118. As the endoscope tip 301 moves, the camera 505 records image frames representing the perspectives visible to the endoscope tip 301. During an image registration process (further described in Section VI. Image Registration), the image registration module 130 can measure translation between the recorded image frames as a function of time. The translations correspond to movement of the tip 301 in the pitch and/or yaw axis, and thus can be used to calibrate the surgical robotics system's pitch and yaw controls.

Figure 5B:
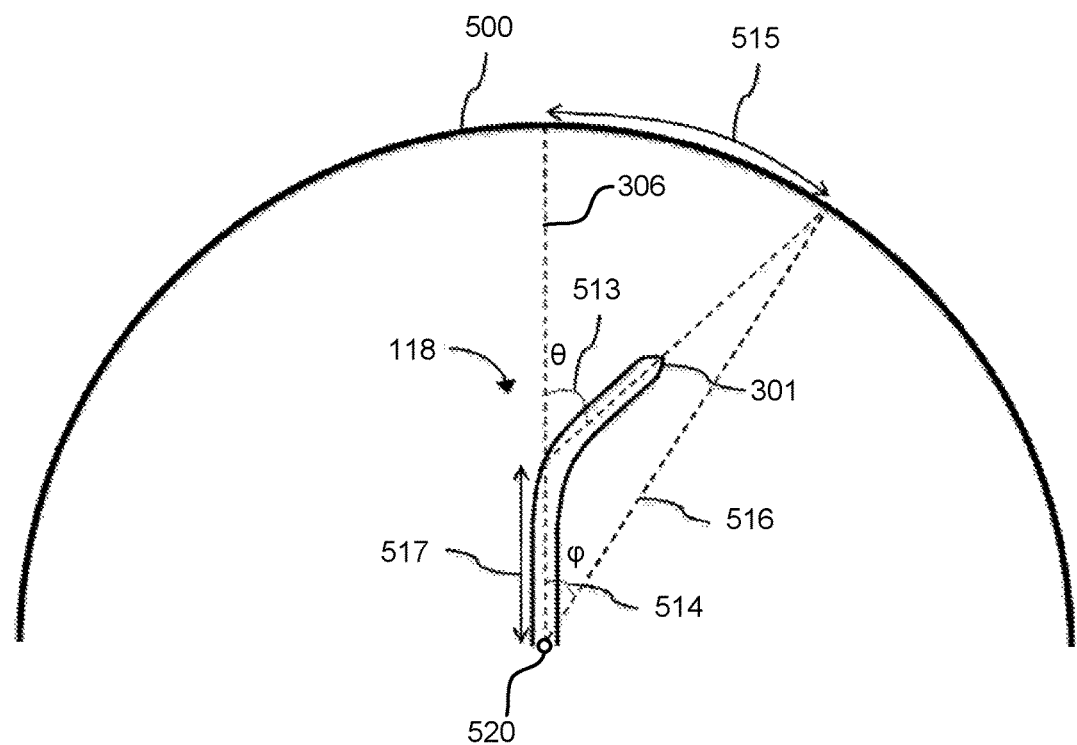
FIG. 5B illustrates the endoscope positioned within a calibration structure according to one embodiment.

FIG. 5B illustrates the endoscope 118 positioned within a calibration structure 500 during calibration according to one embodiment. Though the calibration structure 500 shown in FIG. 5B is a dome, it should be noted that the calibration structure 500 may be a different type of shape in other embodiments. A proximal end of the endoscope 118 is aligned with the center 520 of the calibration structure 500 dome. The tip 301 has been deflected to a positive yaw angle 513, of θ radians relative to the longitudinal axis 306. The positive yaw angle 513 may be related geometrically to the deflection angle 514 of φ radians of the endoscope 118 relative to the longitudinal axis 306. In use cases where the calibration structure 500 is a dome, the deflection angle 514 is determined by dividing the geodesic distance 515 along the surface of calibration structure 500 by the radius 516 of the calibration structure 500. The geodesic distance 515 may be determined using image registration (further described in Section VI. Image Registration) to detect translation between images from a recorded image sequence. The yaw angle 513 (θ) may be calculated based on the deflection angle 514 (φ), the radius 516 (R), and the distance 517 (r) from the center 520 to the yaw angle 513, as shown in the following equation:

$$\theta = \sin^{-1}\frac{R\sin\varphi}{\sqrt{R^2 + r^2 - 2Rr\cos\varphi}}.$$

In cases when r is much smaller than R, the deflection angle 514 (φ) may be an accurate approximation of the yaw angle 513 (θ). The distance (r) may be predetermined based on physical measurements of the endoscope tip 301, or may be calculated during use of the endoscope 118, for example, by measuring changes in distance to a surface of the calibration structure 500 based on detected magnification changes corresponding to image scaling. The negative yaw, positive pitch, and negative pitch angles can be determined using equations similar to the equation shown above.

V. Calibration Curves

Figure 6A:
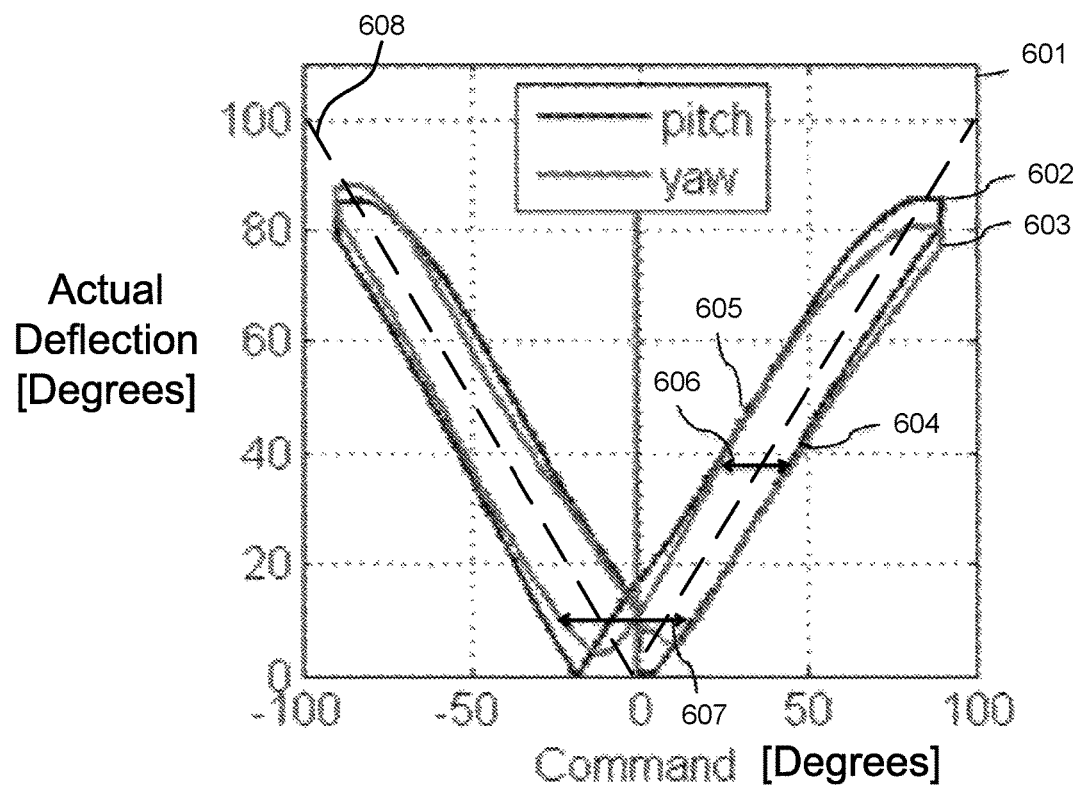
FIG. 6A shows a plot of measured endoscope actual deflection in pitch and yaw in response to a calibration procedure according to one embodiment.

FIG. 6A shows a plot 601 of measured endoscope actual deflection (e.g., articulation angle of the endoscope) in pitch and yaw in response to a calibration procedure according to one embodiment. During the calibration procedure, a surgical robotics system 100 actuates the endoscope 118 shown in FIG. 5A in the negative yaw axis 303, positive yaw axis 302, negative pitch axis 305, and positive pitch axis 304 as shown in FIG. 3A. The calibration module 125 records, using sensors (e.g., image sensors, accelerometers, gyroscopes, strain gauges, etc.) of the surgical robotic system 100 and/or the endoscope 118, the actual deflection of the endoscope 118 (e.g., in units of degrees) in each axis as a function of a corresponding command (e.g., provided by the command console 200 shown in FIG. 2) to generate the two curves 602 and 603 (also referred to as calibration curves) representing the endoscope's actual deflection in the pitch axis and yaw axis, respectively. The command (also referred to as the command value) represents a target deflection, for example in units of degrees. Due to nonlinearities of the endoscope 118, the target deflection of a command does not always match the actual deflection shown on the plot 601. The calibration module 125 can store the actual deflection, as well as other data associated with the calibration procedure such as the corresponding range of command values and the unique identifier of the endoscope 118, in the calibration store 135.

The actual deflection of both curves 602 and 603 exhibit local linearity as the command value increases or decreases, as well as nonlinear behavior. In particular, the forward portion 604 of the curve 602 and backward portion 605 of the curve 602 is offset by hysteresis 606. Likewise, the forward and backward portions of the curve 603 are also offset by a hysteresis. Further, the curves 602 and 603 exhibit a "dead zone" 607 around an actual deflection of zero degrees. In the "dead zone" 607, the endoscope is less sensitive to changes to the command value, e.g., relative to the forward portion 604 and backward portion 605, the actual deflection changes less per unit of change to the command value. For reference, the dashed lines 608 represent an example model without nonlinearities.

The calibration module 125 generates a fit to account for the endoscope's nonlinear behavior. In one embodiment, the fit is a piecewise linear model. The calibration module 125 uses the data from the curves 602 and 603 shown in FIG. 6A to generate the four plots illustrated in FIGS. 6B, 6C, 6D, and 6E corresponding to increasing target deflection in the pitch axis, decreasing target deflection in the pitch axis, increasing target deflection in the yaw axis, and decreasing target deflection in the yaw axis, respectively.

Figure 6B:
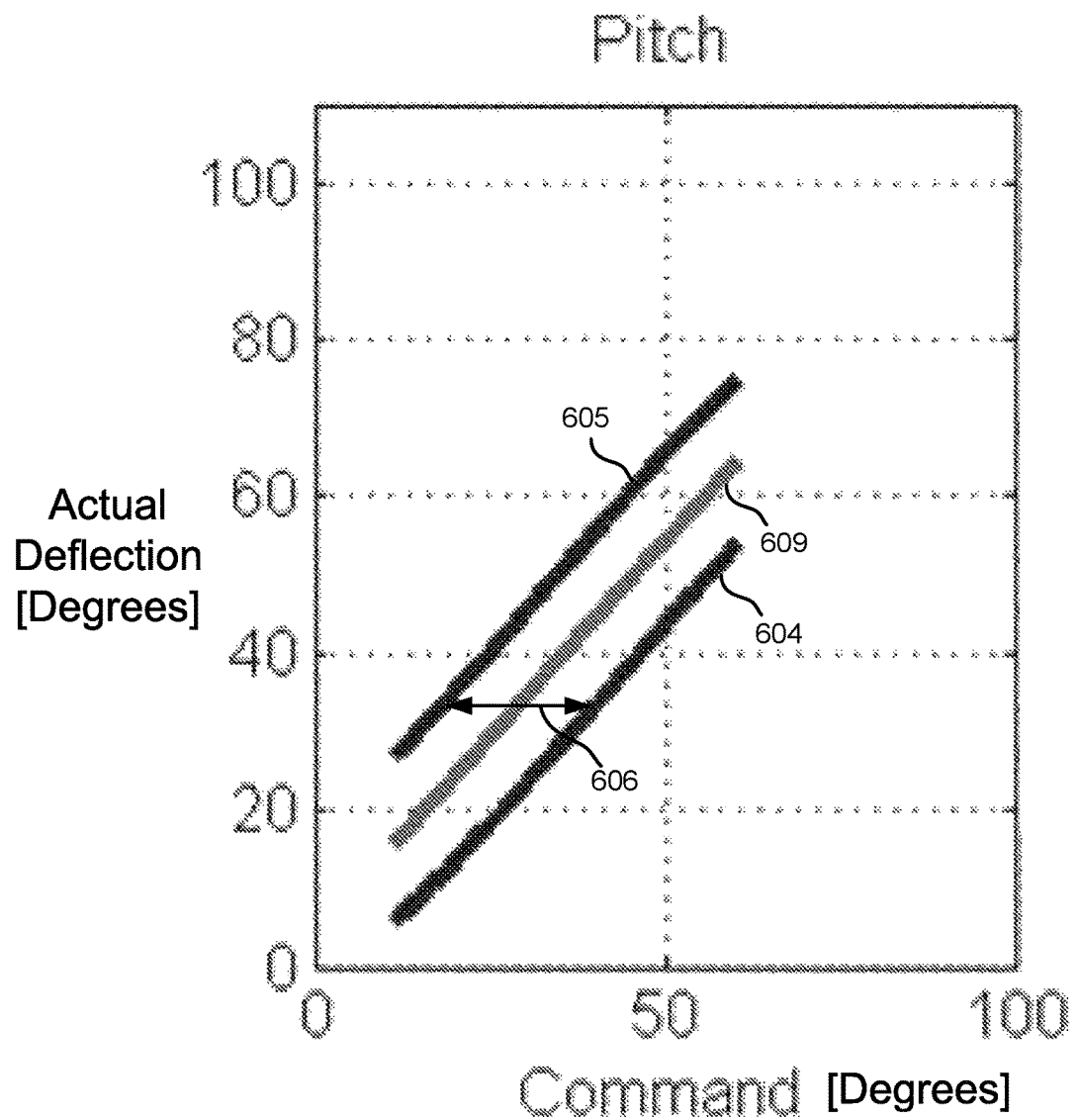
FIG. 6B shows a plot of linear curves corresponding to increasing target deflection in the pitch axis according to one embodiment.

FIG. 6B shows a plot 607 of linear curves corresponding to increasing target deflection in the pitch axis according to one embodiment. The plot 607 includes a segment of the forward portion 604 and a segment of the backward portion 605 of the curve 602 shown in FIG. 6A corresponding to actual deflection in the pitch axis. Based on the two segments, the calibration module 125 determines a linear fit 609 corresponding to the increasing target deflection in the pitch axis. For example, the linear fit 609 is a value of the average (or a weighted average) slope of the two segments. Further, the calibration module 125 determines the hysteresis 606 based on the width of the gap between the two segments. The calibration module 125 can store values associated with the linear fit 609 and the hysteresis 606, collectively referred to as the calibration parameters, in the calibration store 135.

Figure 6C:
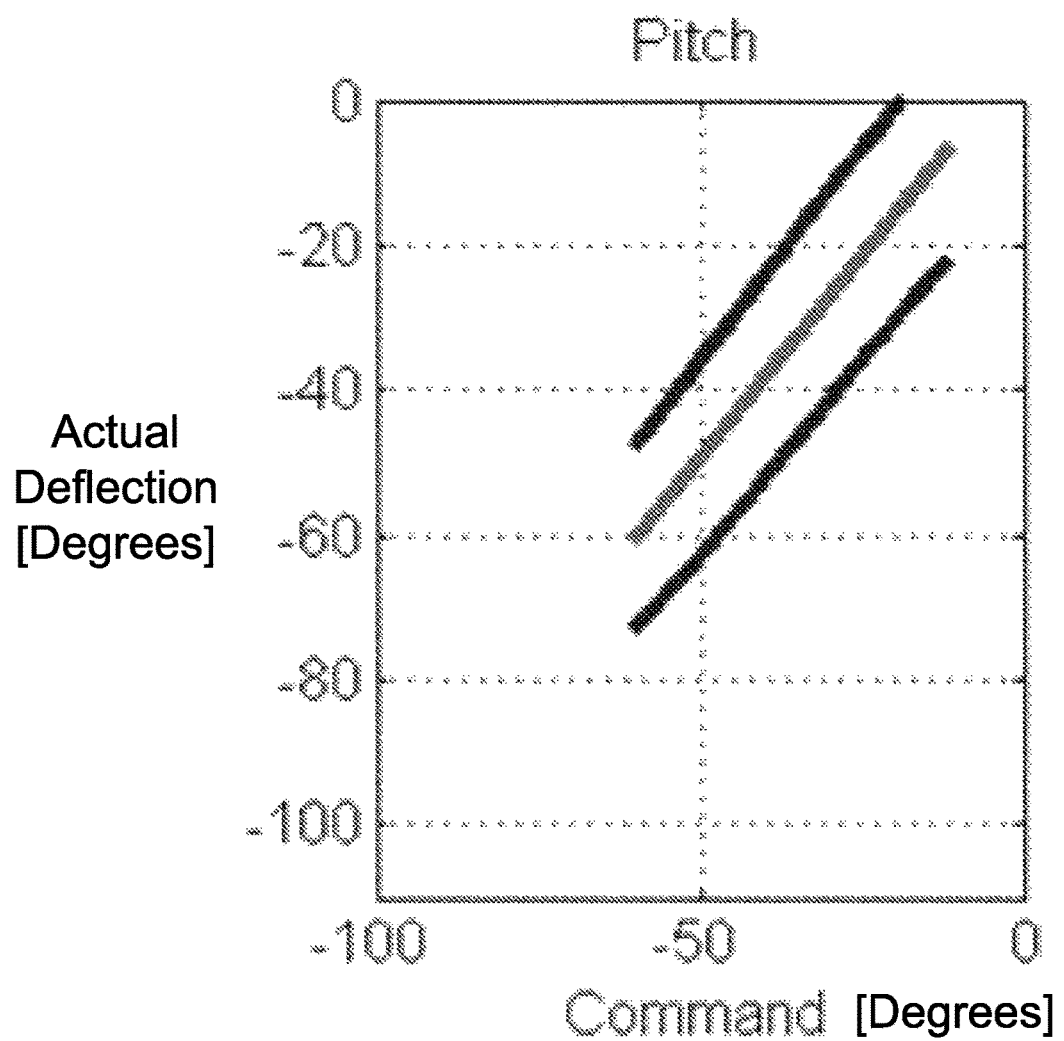
FIG. 6C shows a plot of linear curves corresponding to decreasing target deflection in the pitch axis according to one embodiment.
Figure 6D:
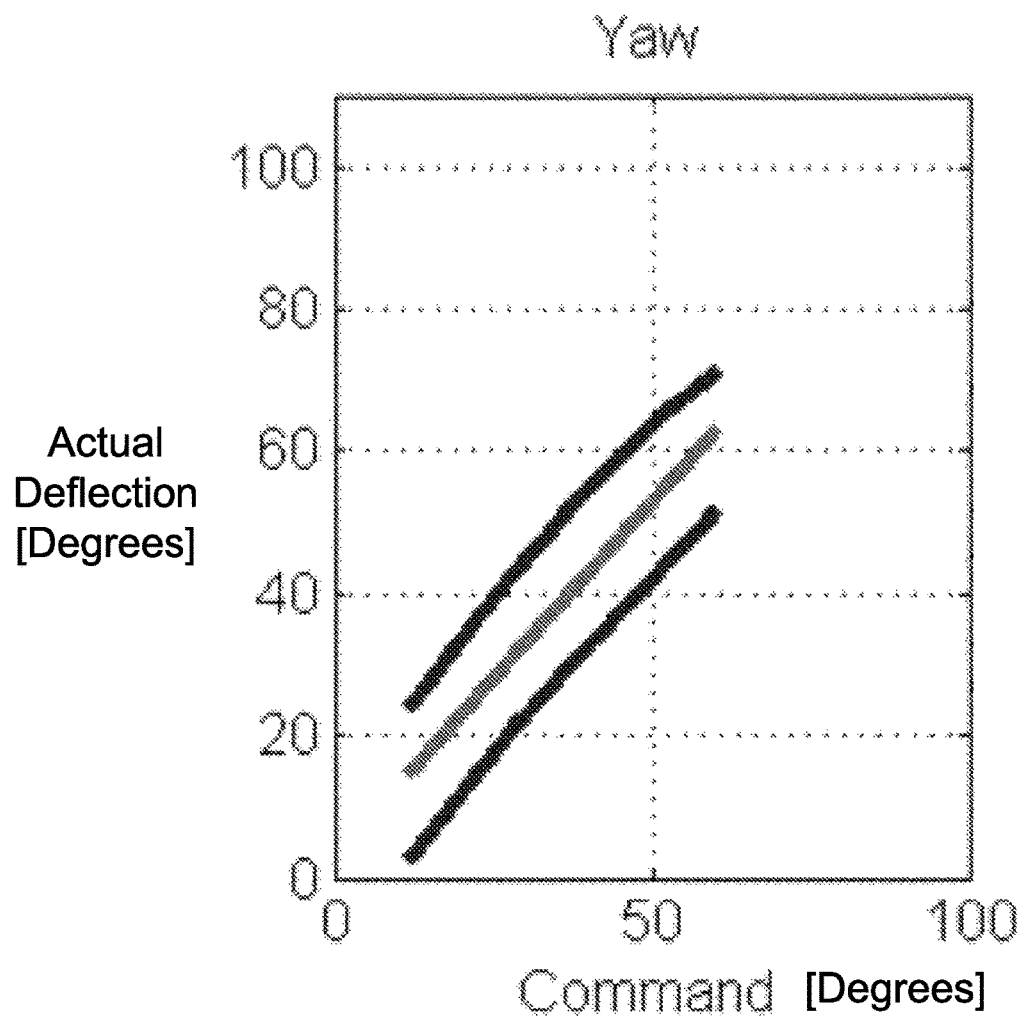
FIG. 6D shows a plot of linear curves corresponding to increasing target deflection in the yaw axis according to one embodiment.
Figure 6E:
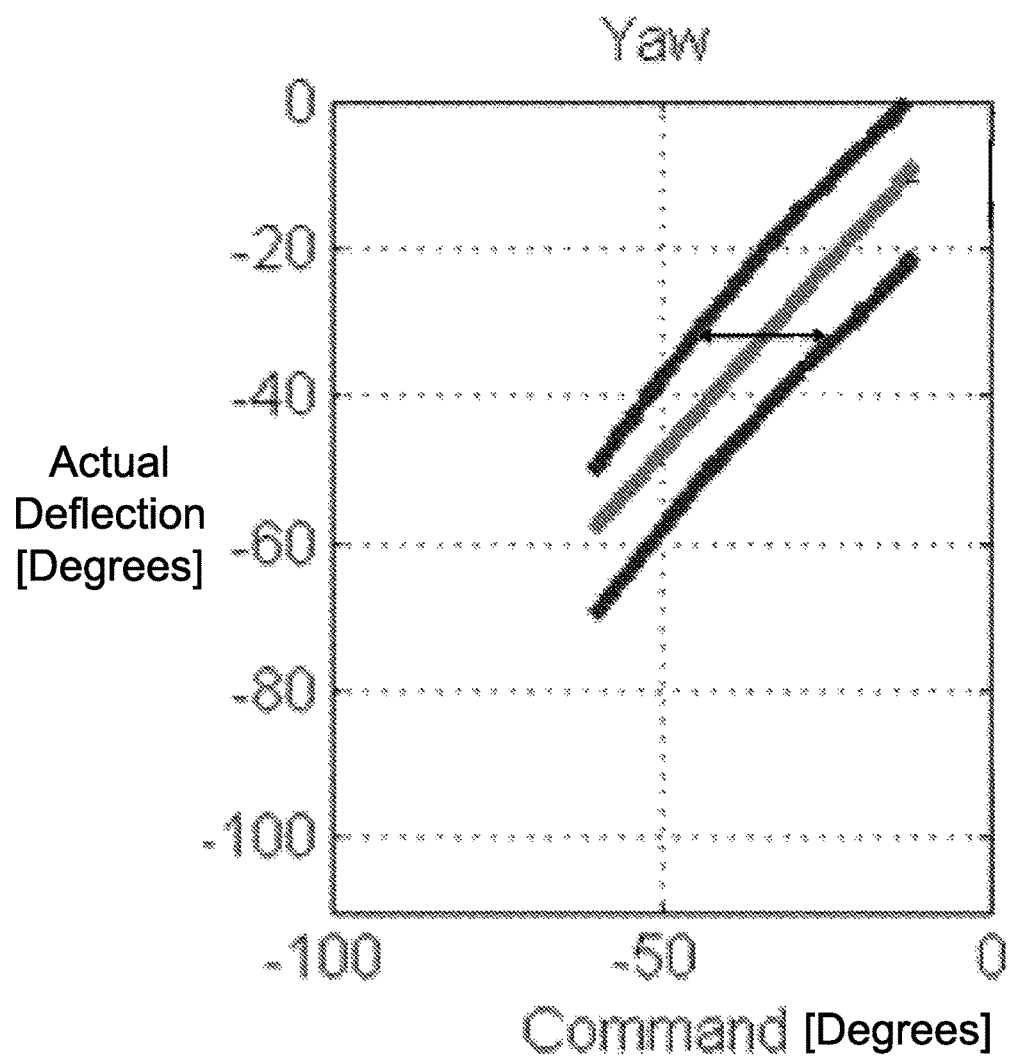
FIG. 6E shows a plot of linear curves corresponding to decreasing target deflection in the yaw axis according to one embodiment.

The calibration module 125 uses a similar process to determine the linear fits and hysteresis for the plots shown in FIGS. 6C-E. FIG. 6C shows a plot of linear curves corresponding to decreasing target deflection in the pitch axis according to one embodiment. FIG. 6D shows a plot of linear curves corresponding to increasing target deflection in the yaw axis according to one embodiment. FIG. 6E shows a plot of linear curves corresponding to decreasing target deflection in the yaw axis according to one embodiment.

VI. Image Registration

Figure 8:
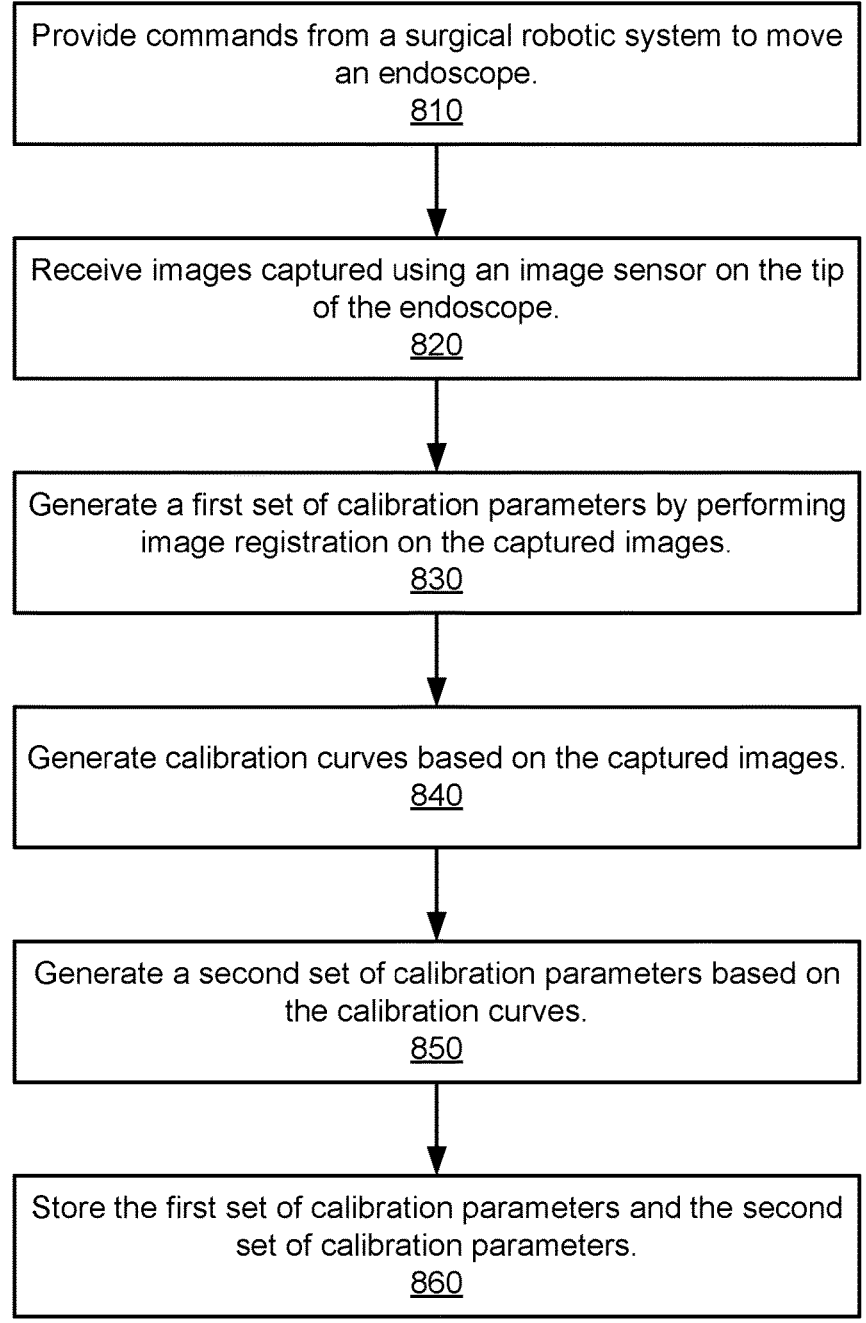
FIG. 8 is a flowchart of a process for automated calibration of an endoscope according to one embodiment.

FIG. 7 is a flowchart of a process 700 that may be performed as part of the process illustrated in FIG. 8 to determine the movements of the endoscope from a sequence of recorded images according to one embodiment. A controller of a surgical robotics system, for example, the controller 120 of the surgical robotics system 100 shown in FIG. 1, uses the process 700 to calibrate an endoscope. The process 700 may include different or additional steps than those described in conjunction with FIG. 7 in some embodiments, or perform steps in different orders than the order described in conjunction with FIG. 7. Since the controller 120 automates the process 700, a user does not have to manually perform a calibration procedure to use the surgical robotic system 100.

The image registration module 130 of the surgical robotic system 100 shown in FIG. 1 determines calibration parameters of an endoscope tip based on changes in properties of a sample of images (e.g., grayscale or color) captured by an image sensor coupled to the endoscope tip, e.g., the camera 505 of endoscope 118 shown in FIG. 5A. Because the image sensor is coupled to the endoscope 118, the image registration module 130 assumes that changes between a pair of images of the sample are due to a shift in perspective of the image sensor corresponding to a movement of the endoscope tip, e.g., translation, rotation, and/or scaling in a pitch or yaw axis.

The image registration module 130 can filter the sample of images, for example, by removing every other image of the sample to help reduce the time required to process the sample. In some embodiments, the image registration module 130 extracts the sample of images from a video captured by the image sensor. Image registration does not require the source and target images to be subsequent frames of the camera. However, the accuracy of the motion estimated by image registration tends to be greater as the time period between images decreases. Thus, the image registration module 130 generates more accurate motion estimates (e.g., nearly continuous measurement of calibration parameters) by registering many images in sequence.

To determine translation movement, the image registration module 130 receives 710 a sample of images and analyzes pairs of images of the sample using an optical flow technique. In a pair of images, the image that occurs first is referred to as the source image and the image that occurs second is referred to as the target image. The order of the first and second images is arbitrary. Thus, the direction of translation (e.g., moving forward or backward in time) is determined based on which image is considered the source and which images is considered the target. In one embodiment, each image is a two-dimensional pixel array of N pixel values corresponding to light intensities (e.g., for grayscale images), vectors representing intensities of different colors of light (e.g., for color images), etc. The image registration module 130 can transform the two-dimensional pixel array into a corresponding 1-dimensional array with N elements for processing.

The image registration module 130 generates 720 a difference array D and generates 730 a gradient array G based on the pair of images. In some embodiments, the image registration module 130 generates a difference array and gradient array for each pair of images of the sample. The difference array D is based on the difference between a pixel value of the target image and a corresponding pixel value of the source image. The gradient array G is based on a weighted average of the rate of change (e.g., derivative) of a pixel value of the target image and the rate of change of a corresponding pixel value of the source image. In embodiments with a two-dimensional (e.g., x and y dimensions) pixel array, the rate of change of a pixel in the x-dimension $G_x$ is based on the difference between the pixel and each of two or more adjacent pixels in the x-direction. Similarly, the rate of change of the pixel in the y-dimension $G_y$ is based on the difference between the pixel and each of two or more adjacent pixels in the y-direction. The gradient array may be a weighted average of the rates of change in the x and y dimensions, e.g., equally weighted. The image registration module 130 can decompose the 2D gradient array into two sub-arrays, $G_x$ and $G_y$, corresponding to partial derivatives in the x and y directions, respectively. Accordingly, the image registration module 130 represents G as an N×2 matrix: $G=(G_x\ G_y)$, where $G_x$ and $G_y$ each include N components.

The image registration module 130 determines a set of calibration parameters represented by the vector p. In some embodiments, the image registration module 130 determines a set of calibration parameters for each image pair based on the gradient array G and difference array D. The image registration module 130 can repeat the steps 720-750 of the process 700 for multiple pairs of images of the sample. Thus, the image registration module 130 generates a set of calibration parameters corresponding to each processed pair of images.

The vector p includes a set of model parameters (e.g., representing different types of movement of the endoscope tip) and can be modeled as satisfying a linear equation of the form: $Ap=v$, where $A=(G_x\ G_y)$, $v=D$. The image registration module 130 can use a least squares regression analysis to estimate that $p=(A^TA)^{-1}A^Tv$, where $A^T$ represents the transpose of A and $(A^TA)^{-1}$ represents the inverse of the product of $A^T$ with A. Thus, the image registration module 130 determines that $$p = \begin{pmatrix} t_x \\ t_y \end{pmatrix},$$

where $t_x$ and $t_y$ represent translational movement of the endoscope tip in the x and y dimensions, respectively.

The image registration module 130 can also determine rotational movement of the endoscope tip corresponding to an angle of rotation, θ. For example, the image registration module 130 may represent p as a two-dimensional vector of the form $$p = \begin{pmatrix} a \\ b \end{pmatrix},$$

where b represents the sine of the angle of rotation (e.g., θ) and a represents the square of the cosine of the angle of rotation (e.g., θ) minus 1. Note that for small angles of rotation, b≈θ and a will be small (a≈−θ²). The image registration module 130 determines a matrix A=($G_x r_x + G_y r_y$, $G_x r_y - G_y r_x$), where the vectors $r_x$ and $r_y$ denote the positions of a given pixel relative to the center of rotation. The image registration module 130 determines p to estimate the angle of rotation by solving the equation Ap=v. In cases where a source image has been scaled, for example, due to a change in distance from the source image to the target image, the image registration module 130 determines the scale factor s based on the equations: $s^2 = (a+1)^2 + b^2$, and $b/s = \sin\theta \approx \theta$.

The image registration module 130 can generate a matrix A that combines the translational and rotational movement components as shown below:

$$A = (G_x r_x + G_y r_y \quad G_x r_y - G_y r_x \quad G_x \quad G_y) \text{ and } p = \begin{pmatrix} a \\ b \\ t_x \\ t_y \end{pmatrix};$$

The image registration module 130 can transform A using an arbitrary matrix of the form $$A = (G_x r_x \quad G_x r_y \quad G_y r_x \quad G_y r_y) \text{ and } p = \begin{pmatrix} a \\ b \\ c \\ d \end{pmatrix}.$$

resulting in:

$$\begin{pmatrix} 1+a & b \\ c & 1+d \end{pmatrix}.$$

The image registration module 130 uses the calibration parameters p to generate a sequence of transforms $T_i$, where $T_i$ represents a transform from the ith to the (i+1)th image of a sample. The vector $p_n$ includes the calibration parameters for the nth image, and the vector $p_{n+1} = T_n p_n$ includes the calibration parameters for the (n+1)th image. $T_i$ may indicate motion in one or more axis between images.

To obtain the calibration parameters p as a function of image number, the image registration module 130 applies the transforms sequentially to a starting vector $p_1$, so that p of an arbitrary image n is:

$$p_n = \left( \prod_{i=1}^{n-1} T_i \right) p_1.$$

Generally, $T_i$ does not commute, so each $T_i$ is applied in order starting with $T_1$. The sequential measurements of $p_i$ may represent a trajectory, for example, a movement from an initial position or orientation $p_1$ continuously through a series of positions or orientations to a final position or orientation $p_n$. Thus, the image registration module 130 can determine an unknown p for an arbitrary image using a known p for a starting image and applying a sequence of known transformations using the equation shown above. The calibration parameters may include measurements in units of pixels. The image registration module 130 can convert the units using conversion factors. For example, an object of known size in millimeters in an image is measured in pixels to determine a conversion factor from millimeters to pixels.

In some embodiments, the image sensor includes one or more color channels, e.g., three color channels corresponding to red, green, and blue (RGB) light colors. Since each color channel may be sensitive to different colors, more accurate measurements during a calibration process may be obtained using a multi-colored target. For example, the surface of a calibration structure such as the dome calibration structure 500 shown in FIG. 5A includes a patterned surface of multiple colors, e.g., an alternating pattern of red and green checkered squares. The image registration module 130 represents color images using an additional dimension. Further, the image registration module 130 can independently determine the matrices $A_i$ and vectors $v_i$ for each color channel i in the same manner as A and v as described above. The image registration module 130 may concatenate $A_i$ and $v_i$ into matrices A and v:

$$A = \begin{pmatrix} A_1 \\ \vdots \\ A_M \end{pmatrix}; v = \begin{pmatrix} v_1 \\ \vdots \\ v_M \end{pmatrix}.$$

The calibration parameters may be more sensitive to certain color channels. For example, in RGB images of a calibration structure surface that includes red and green colored squares, the calibration parameters are more sensitive to the red and green channels than the blue channel. Image data from the blue channel may predominantly represent noise, while image data from the red and green channels may represent signal. The image registration module 130 can adjust the sensitivity of a color channel by applying 740 weights to the difference array and/or the gradient array. For example, for each color channel, the image registration module 130 multiplies each matrix $A_i$ and vector $v_i$ by an independently-variable vector of weighting parameters $w_i$ prior to concatenation:

$$A = \begin{pmatrix} w_1 A_1 \\ \vdots \\ w_M A_M \end{pmatrix}; v = \begin{pmatrix} w_1 v_1 \\ \vdots \\ w_M v_M \end{pmatrix}.$$

The image registration module 130 generates 750 a set of calibration parameters based on the difference array and the gradient array. The calibration parameters corresponding to the weighted versions of A and v are more dependent on the color channels with larger weight than those with smaller weight. For example, to produce calibration parameters that respond equally strong to red and green color channels, but weak to the blue color channel, the weight for the red and green channels is 1, and the weight for the blue channel is 0.05. The weighting parameters may be adjusted to account for a wide range of experimental variables, including camera sensitivity, target pattern color of a calibration structure, or the color of illuminating light. In some embodiments, the image registration module 130 further customizes the sensitivity of the set of calibration parameters by using other types of weighting methods, e.g., nonlinear weighting functions or weighting functions based on variables such as pixel location.

VII. Process Flows

FIG. 8 is a flowchart of a process 800 for automated calibration of an endoscope according to one embodiment. The process 800 may include different or additional steps than those described in conjunction with FIG. 8 in some embodiments, or perform steps in different orders than the order described in conjunction with FIG. 8. Since the controller 120 is capable of automating the process 800, a user does not have to manually perform a calibration procedure to use the surgical robotic system 100. Automated calibration is advantageous, e.g., because the process reduces the time required to calibrate an endoscope.

The calibration module 125 of the controller 120 provides 810 one or more commands from the surgical robotic system 100 to an actuator, for example, the IDM 117 shown in FIG. 1, to move the endoscope 118 for a calibration procedure. The endoscope may be positioned in a calibration structure (e.g., calibration structure 500 shown in FIG. 5A) during the calibration procedure. Based on the commands, the IDM 117 moves the endoscope in a translational and/or rotational motion in one or more axis, e.g., the positive yaw axis 302, negative yaw axis 303, positive pitch axis 304, negative pitch axis 305, or roll axis 306 shown in FIG. 3A.

The calibration module 125 receives 820 images captured using an image sensor on the tip (e.g., tip 301 shown in FIG. 3A) of the endoscope 118. The images may include a sample of one or more adjacent images (i.e., in sequence) or non-adjacent images. The images correspond to a movement of the endoscope 118. For example, the calibration module 125 provides the commands to the IDM 117 in step 710 and simultaneously (or soon afterwards) provides a coordinated command to the endoscope 118 to capture the images using the image sensor.

The image registration module 130 of the controller 120 generates 830 a first set of calibration parameters by performing image registration on the captured images, as previously described in Section VI. Image Registration. The first set of calibration parameters can include values representing translational and/or rotational movement of the endoscope tip 301 in one or more axis, e.g., pitch and/or yaw.

The calibration module 125 generates 840 a model of the endoscope's movements based on the captured images. In an example use case, during the step 710, the IDM 117 moves the endoscope forward and backward in both a pitch axis and a yaw axis. The resulting model can be illustrated by the calibration curves 602 and 603 as shown in plot 601 in FIG. 6A representing the endoscope's motion in the pitch and yaw axis, respectively. Each calibration curve may be associated with an axis of motion of the endoscope 118.

The calibration module 125 generates 850 a second set of calibration parameters based on the calibration curves. Following in the same example use case, the calibration module 125 uses curve fitting to determine values for a slope, hysteresis, and/or "dead zone" to include in the second set of calibration parameters. For example, the values may be based on the calibration curves 602 and 603, as shown in the plots in FIGS. 6A-E. The plots in FIGS. 6B-E each represent a linear portion of a calibration curve of the plot 601 corresponding to one of: increasing articulation angle in the pitch axis, decreasing articulation angle in the pitch axis, increasing articulation angle in the yaw axis, and decreasing articulation angle in the yaw axis.

The calibration module 125 stores 860 the first set of calibration parameters and/or the second set of calibration parameters in the calibration store 135 or any other database accessible to the surgical robotic system 100. The calibration module 125 may store the sets of calibration parameters with a unique identifier associated with the given endoscope 118. In some embodiments, the calibration store 135 includes a lookup table that stores calibration parameters mapped to unique identifiers. Thus, the calibration module 125 can retrieve a calibration parameters associated with a given endoscope using the lookup table with an input unique identifier. In some embodiments, the calibration module 125 stores the sets of calibration parameters with a type of command (e.g., translation or rotation in a given axis) corresponding to the commands used to move the endoscope 118 in step 810.

Figure 9:
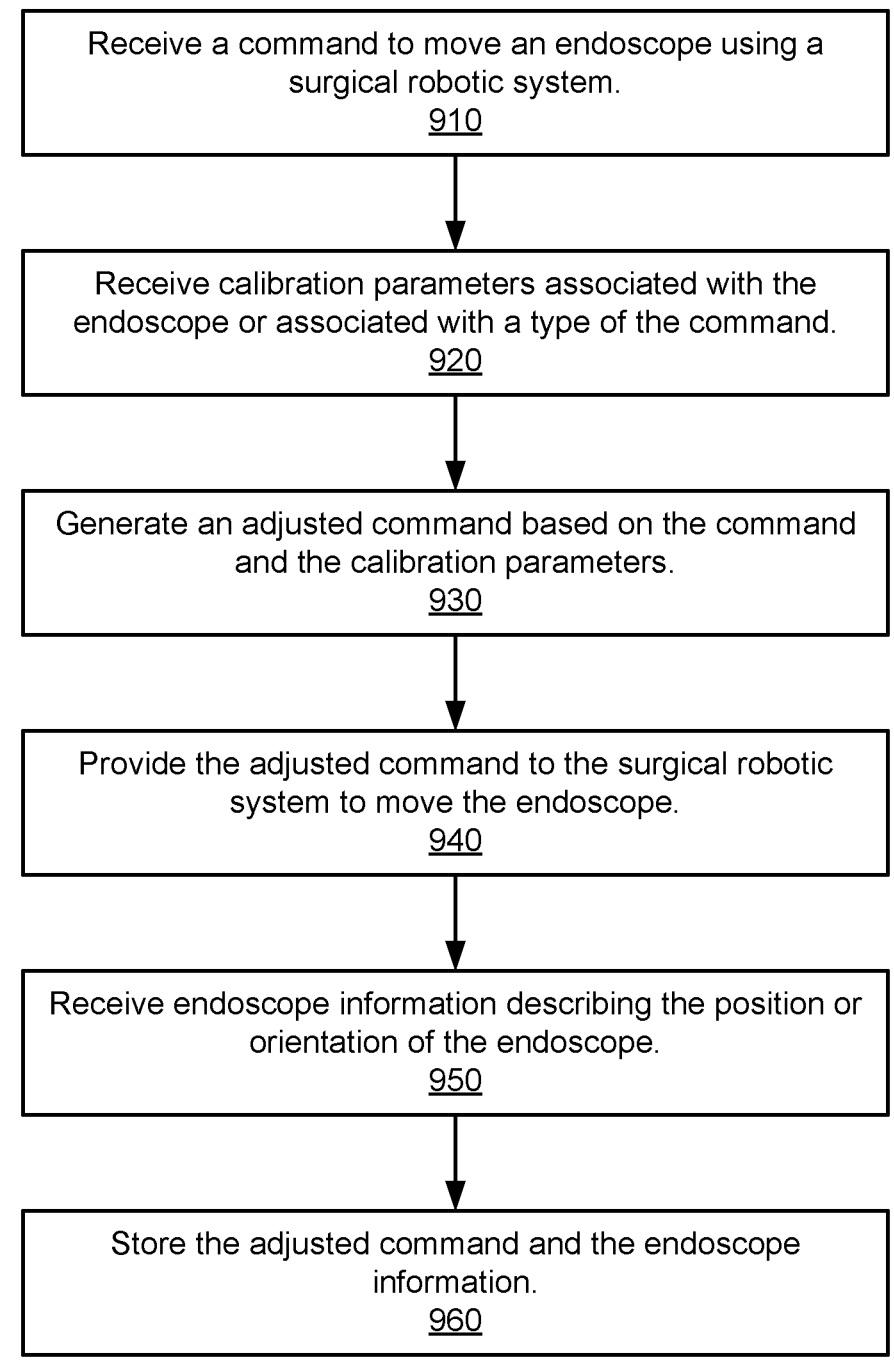
FIG. 9 is a flowchart of a process for controlling an endoscope using calibration parameters, according to one embodiment.

FIG. 9 is a flowchart of a process 900 for controlling an endoscope using calibration parameters, according to one embodiment. The process 900 may include different or additional steps than those described in conjunction with FIG. 9 in some embodiments, or perform steps in different orders than the order described in conjunction with FIG. 9. The command console, such as command console 200, may use the process 900 in the velocity mode or position control mode previously described in Section II. Command Console.

The command console 200 receives 910 a command to move the endoscope 118 using the surgical robotic system 100, e.g., using the robotic arms 102 and the IDM 117 shown in FIG. 1. The command may cause the endoscope 118 and the tip 301 of the endoscope (as shown in FIG. 3A), to translate or rotate in one or more axis. The command can be received from a user of the surgical robotic system 100 via the control modules 203 and 204 shown in FIG. 2. In other embodiments, commands can be received from a processor or database of the surgical robotic system 100, e.g., a pre-programmed routine of motion commands associated with a surgical procedure.

The command console 200 receives 920 calibration parameters associated with the endoscope 118 or associated with a type of the command. The calibration parameters may include calibration parameters generated using the process 700 shown in FIG. 7 using image registration (e.g., by generating difference arrays and gradient arrays). The calibration parameters may also include calibration parameters generated using the process 800 shown in FIG. 8 using calibration curve fitting. The command console 200 generates 930 an adjusted command based on the command and the calibration parameters. The adjusted commands account for nonlinear behavior (e.g., corresponding to translational and/or rotational motion in one or more axis) of the endoscope 118 using the calibration parameters. In an example use case, the command describes a translational motion of 10 degrees in the positive pitch axis and 20 degrees in the positive yaw axis. Due to nonlinearities of the endoscope 118, the endoscope 118 instead translates 5 degrees in the positive pitch axis and 30 degrees in the positive yaw axis based on the command. The calibration parameters indicate that the translation in the positive pitch axis undershoots by 5 degrees and the translation in the positive yaw axis overshoots by 10 degrees. Thus, the adjusted command describes a translational motion of 15 degrees in the positive pitch axis and 10 degrees in the positive yaw axis to compensate for the nonlinearities.

In embodiments where the calibration parameters include both a first set of calibration parameters (generated using image registration) and a second set of calibration parameters (generated using calibration curve fitting), the command console 200 generates the adjusted command by combining different types of calibration parameters. For example, calibration parameters generated using image registration includes translations and rotations. In addition, calibration parameters generated using the calibration curve fitting process includes slopes and hysteresis. The command console 200 can first apply a translation from the first set to modify the command and then apply a hysteresis from the second set to modify the command again, resulting in the final adjusted command. In other embodiments, the command console 200 applies any number of different calibration parameters from one or both sets in any particular order.

The command console 200 provides 940 the adjusted command to the surgical robotic system 100 to move the endoscope 118.

The command console 200 receives 950 endoscope information describing the position or orientation of the endoscope 118, e.g., in response to the surgical robotic system 100 to moving the endoscope 118 based on the adjusted command. The endoscope information may be captured by sensors (e.g., accelerometers, gyroscopes, etc.) of the robotic arms 102 or other sensors such as the strain gauge 434 of the IDM 117 shown in FIG. 4D.

The command console 200 stores 960 the adjusted command and the endoscope information in the calibration store 135 of the controller 120 shown in FIG. 1 or any other database accessible to the surgical robotic system 100. The command console 200 can use the endoscope information to determine whether the calibration parameters correctly accounted for nonlinearities of the endoscope 118.

Continuing with the same example use case, the endoscope information indicates that the endoscope 118 translated 9 degrees in the positive pitch axis and 21 degrees in the positive yaw axis based on the adjusted command. Since the original command corresponded to translations of 10 degrees in the positive pitch axis and 20 degrees in the positive yaw axis, the endoscope 118 still undershot by 1 degree in the positive pitch axis and overshot by 1 degree in the positive yaw axis. Thus, the command console 200 determines that the calibration parameters did not fully account for the endoscope's nonlinearities.

The command console 200 can use the endoscope information to implement feedback control of the endoscope 118. Particularly, the command console 200 can modify the adjusted command based on the endoscope information. For example, since the endoscope information indicated that endoscope 118 undershot by 1 degree in the positive pitch axis, the command console 200 modifies the adjusted command to translate the endoscope 118 by an additional 1 degree in the positive pitch axis to compensate for the difference. The command console 200 can upload the endoscope information and the adjusted command to a global calibration database including aggregate information from multiple endoscopes and surgical robotic systems.

VIII. Endolumenal Procedures

The surgical robotic system 100 can use stored calibration parameters to perform surgical procedures on a patient. FIGS. 10A-C and FIGS. 11A-C illustrate example surgical procedures using an endoscope, e.g., endoscope 118 shown in FIG. 3A. The calibration parameters allow the surgical robotic system 100 to more accurately navigate the endoscope inside the patient to perform the surgical procedures.

Figure 10A:
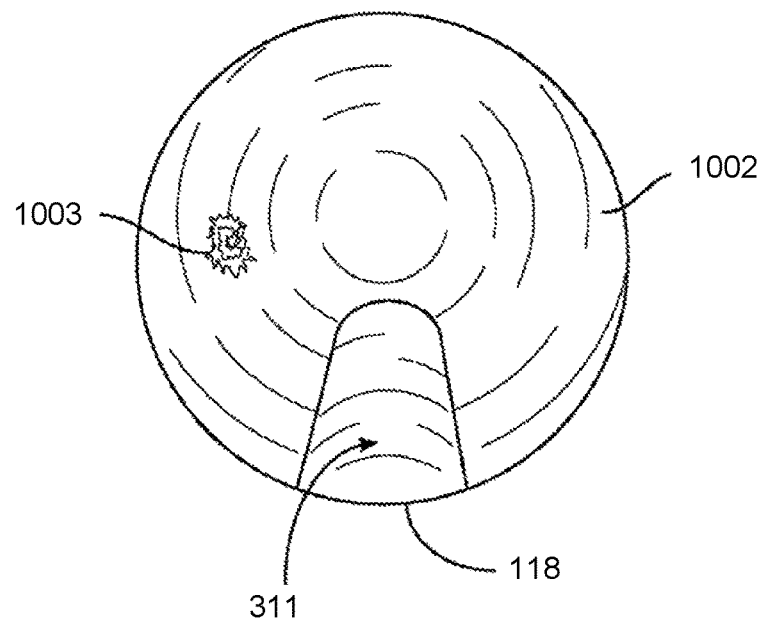
FIG. 10A illustrates the distal end of an endoscope within an anatomical lumen according to one embodiment.

FIG. 10A illustrates the distal end of the endoscope 118 within an anatomical lumen 1002 according to one embodiment. The endoscope 118 includes a sheath 311 and navigates through the anatomical lumen 1002 inside a patient toward an operative site 1003 for a surgical procedure.

Figure 10B:
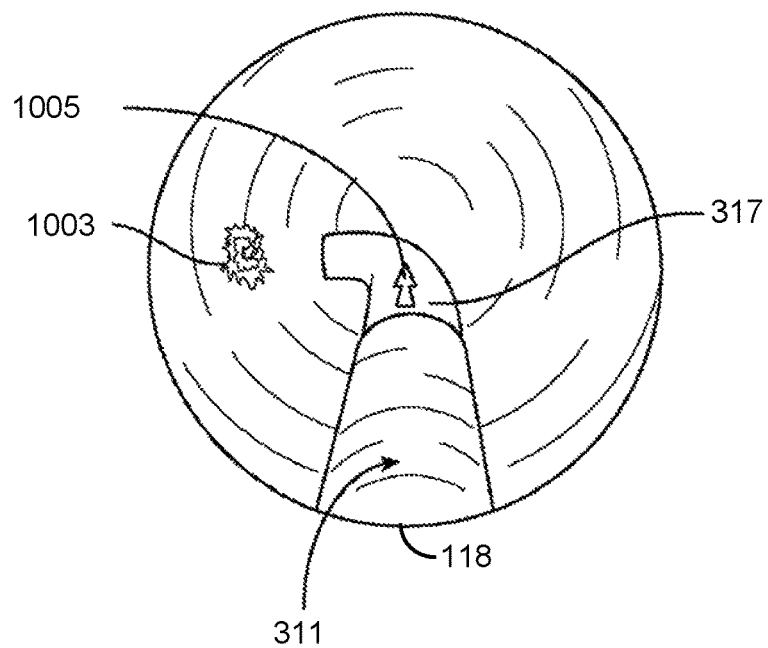
FIG. 10B illustrates the endoscope shown in FIG. 10A in use at an operative site according to one embodiment.

FIG. 10B illustrates the endoscope 118 shown in FIG. 10A in use at the operative site 1003 according to one embodiment. After reaching the operative site 1003, the endoscope 118 extends a distal leader section 317, longitudinally aligned with the sheath 311, in the direction marked by arrow 1005. The endoscope can also articulate the distal leader section 317 to direct surgical tools toward the operative site 1003.

Figure 10C:
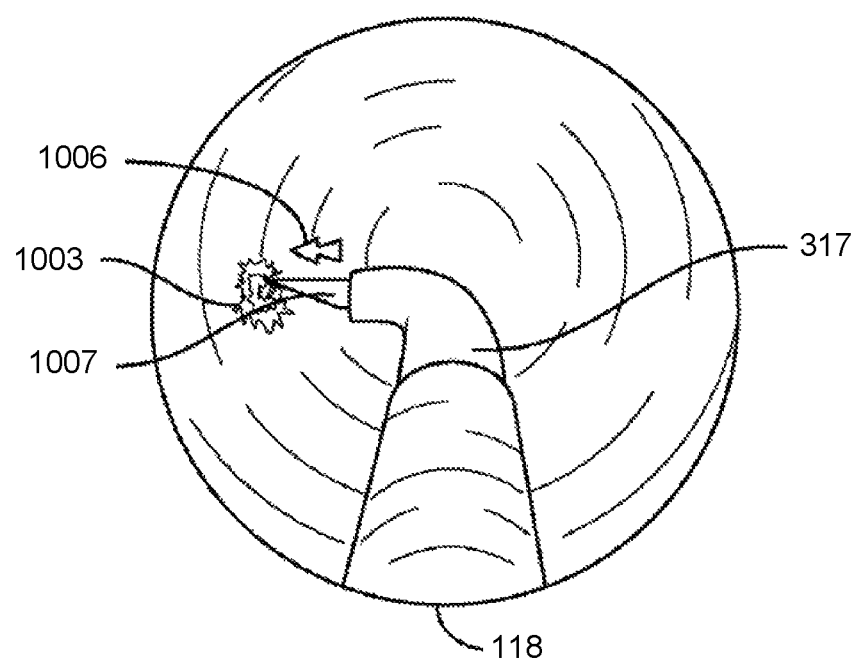
FIG. 10C illustrates the endoscope shown in FIG. 10B with an aspiration needle according to one embodiment.

FIG. 10C illustrates the endoscope 118 shown in FIG. 10B with an aspiration needle 1007 according to one embodiment. In cases where the operative site 1003 includes a lesion for biopsy, the distal leader section 317 articulates in the direction marked by arrow 1006 to convey the aspiration needle 1007 to target the lesion.

Figure 11A:
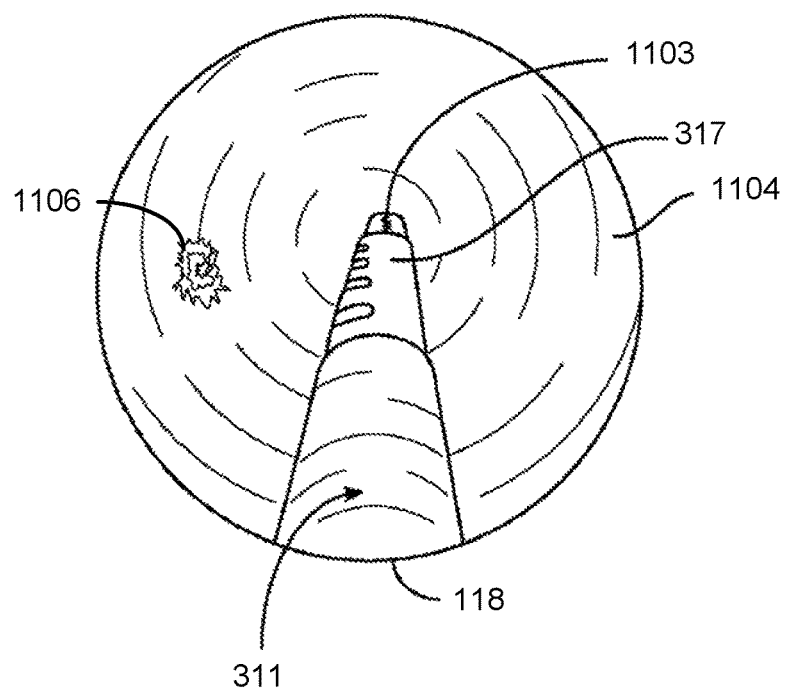
FIG. 11A illustrates an endoscope coupled to a distal flexure section within an anatomical lumen according to one embodiment.

FIG. 11A illustrates an endoscope 118 coupled to a distal leader section 317 within an anatomical lumen 1104 according to one embodiment. The endoscope 118, including a sheath 311, distal leader section 317, and forceps 1103, navigates through the anatomical lumen 1104 toward an operative site 1106. In some embodiments, the distal leader section 317 is retracted within the sheath 311. The construction, composition, capabilities, and use of distal leader section 317, which may also be referred to as a flexure section, are disclosed in U.S. patent application Ser. No. 14/201,610, filed Mar. 7, 2014, and U.S. patent application Ser. No. 14/479,095, filed Sep. 5, 2014, the entire contents of which are incorporated by reference.

The distal leader section 317 can be deployed through a working channel that is off-axis (neutral axis) of the sheath 311, which allows the distal leader section 317 to operate without obscuring an image sensor (not shown in FIG. 11A) coupled to the end of the sheath 311 (or any other location of the endoscope 118). This arrangement allows the image sensor to capture images inside the anatomical lumen 1104 while the endoscope 118 articulates the distal leader section 317 and keeps the sheath 311 stationary.

Figure 11B:
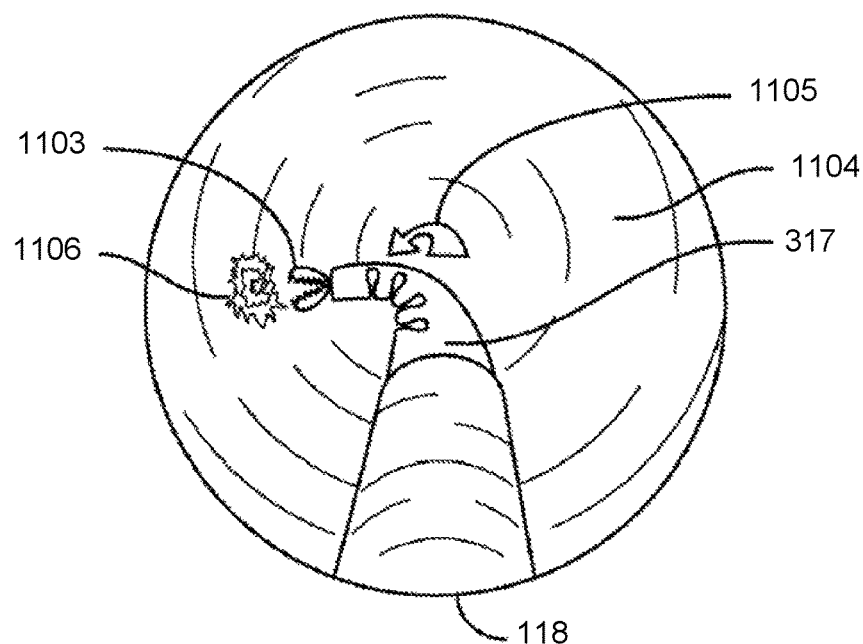
FIG. 11B illustrates the endoscope shown in FIG. 11A with a forceps tool in use at an operative site according to one embodiment.

FIG. 11B illustrates the endoscope shown in FIG. 11A with the forceps 1103 in use at the operative site 1106 according to one embodiment. The endoscope 118 articulates the distal leader section 317 in the direction of arrow 1105 to orient the forceps 1103 toward the operative site 1106. The forceps 1103 takes a biopsy of anatomical tissue at the operative site 1106, e.g., for intraoperative evaluation of the patient. In other embodiments, the endoscope 118 includes a surgical tool different than the forceps 1103, for example graspers, scalpels, needles, probes, or laser devices, which is further described below. The endoscope 118 can substitute the surgical tool intra-operatively to perform multiple functions in a single surgical procedure inside an anatomical lumen.

Figure 11C:
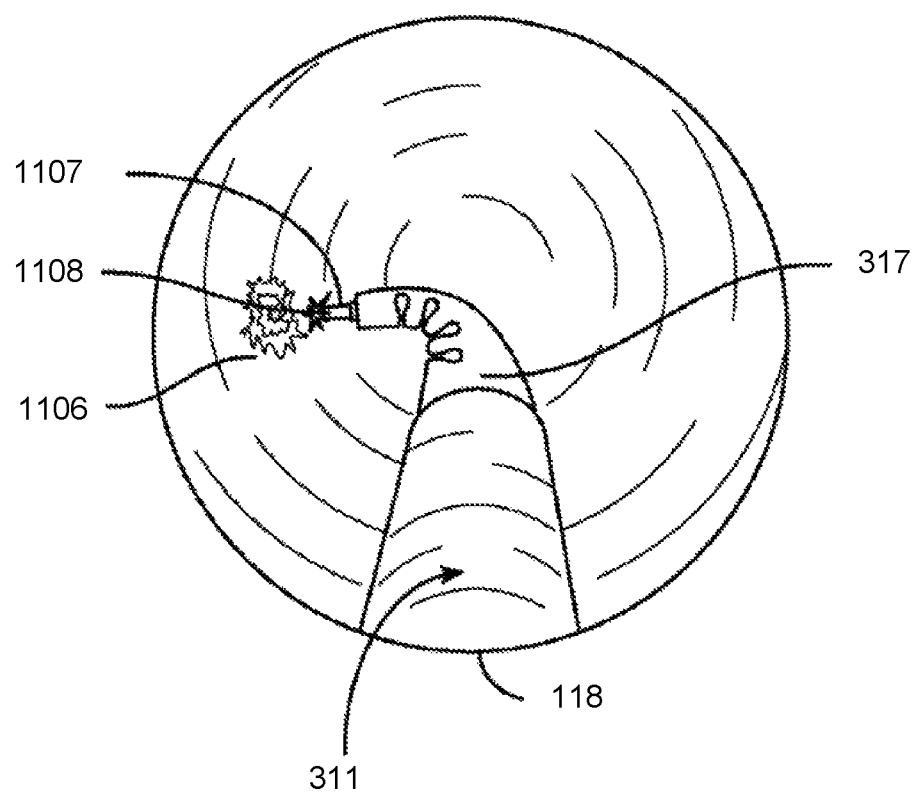
FIG. 11C illustrates the endoscope shown in FIG. 11A with a laser device in use at an operative site according to one embodiment.

FIG. 11C illustrates the endoscope 118 shown in FIG. 11A with a laser device 1107 in use at an operative site according to one embodiment. The laser device 1107 emits laser radiation 1108 at the operative site 1106 for tissue ablation, drilling, cutting, piercing, debriding, cutting, or accessing non-superficial tissue.

IX. Alternative Considerations

Upon reading this disclosure, those of skill in the art will appreciate still additional alternative structural and functional designs through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context unless otherwise explicitly stated.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

What is claimed is:

1. A method for controlling an endoscope of a surgical robotic system, comprising:
    receiving a command to move the endoscope using the surgical robotic system;
    accessing a set of calibration parameters associated with the endoscope, the set of calibration parameters including at least a first set of calibration parameters based on an image registration process using a plurality of images captured by an image sensor coupled to a tip of the endoscope during a calibration procedure that comprises movement of the endoscope between images captured by the image sensor, the calibration procedure including generating a difference array based on differences between images capture by the image sensor between movement of the endoscope performed before receiving the command to move the endoscope and generating a gradient array based on rates of change between the images captured by the image sensor;
    generating an adjusted command based on the command and the set of calibration parameters;
    providing the adjusted command to the surgical robotic system to move the endoscope; and
    receiving movement information describing motion of the endoscope in response at least to the adjusted command.

2. The method of claim 1, wherein the movement information is received from a strain gauge of an instrument device manipulator of the surgical robotic system.

3. The method of claim 1, wherein the set of calibration parameters describes nonlinear behavior of the endoscope and includes:
    a second set of calibration parameters based on a calibration curve fitting process using previously recorded movement information of the endoscope.

4. The method of claim 3, wherein the nonlinear behavior is based at least in part on a stiffness and a length of a helix section of the endoscope.

5. The method of claim 3, wherein generating the adjusted command comprises:
    modifying the command based on at least one calibration parameter from the first set; and
    modifying the command based on at least one calibration parameter from the second set.

6. The method of claim 3, wherein the plurality of images includes information about a pattern on a surface of a dome-shaped calibration structure.

7. The method of claim 1, wherein the image registration process using the plurality of images comprises:
    generating the difference array based on differences in pixel values between a first image of a pair and a second image of the pair;
    generating the gradient array based on rates of change in pixel values between a first image of the pair and a second image of the pair; and
    wherein the first set of calibration parameters is based at least in part on the difference arrays and the gradient arrays.

8. The method of claim 7, wherein the image sensor includes a plurality of color channels and wherein the image registration process using the plurality of images further comprises applying a weighted average to the difference arrays and the gradient arrays based on a sensitivity of each of the color channels.

9. The method of claim 3, wherein the movement information includes at least:
    a first segment describing motion of the endoscope in a forward direction along an axis; and
    a second segment describing motion of the endoscope in a backward direction along the axis.

10. The method of claim 9, wherein the calibration curve fitting process using previously recorded movement information comprises:
    generating a slope by averaging a first rate of change of position of the endoscope based on the first segment and a second rate of change of position of the endoscope based on the second segment;
    generating a hysteresis by determining a difference between the first segment and the second segment; and
    wherein the second set of calibration parameters includes the slope and the hysteresis.

11. The method of claim 1, wherein the endoscope in configured to move in one or more axes including at least a pitch axis and a yaw axis, and wherein the command includes at least a translational motion and a rotational motion.

12. A surgical robotic system, comprising:
    an endoscope;

a robotic arm including a drive mechanism, the drive mechanism coupled to the endoscope; and a controller configured to:

receive a command to move the endoscope using the surgical robotic system;

access a set of calibration parameters associated with the endoscope, the set of calibration parameters including at least a first set of calibration parameters based on an image registration process using a plurality of images captured by an image sensor coupled to a tip of the endoscope during a calibration procedure that comprises movement of the endoscope between images captured by the image sensor, the calibration procedure including generating a difference array based on differences between images capture by the image sensor between movement of the endoscope performed before receiving the command to move the endoscope and generating a gradient array based on rates of change between the images captured by the image sensor;

generate an adjusted command based on the command and the set of calibration parameters;

provide the adjusted command to the surgical robotic system to move the endoscope; and receive movement information describing motion of the endoscope in response at least to the adjusted command.

13. The system of claim 12, wherein the endoscope includes a sheath tubular component coupled to a leader tubular component, the leader tubular component including a helix section.

14. The system of claim 12, wherein the set of calibration parameters is based on an image registration process and calibration curve fitting process, and wherein the set of calibration parameters describe nonlinear behavior of the endoscope.

* * * * *